(12) United States Patent
Verma et al.

(10) Patent No.: US 12,194,244 B2
(45) Date of Patent: Jan. 14, 2025

(54) HUMIDIFIER RESERVOIR

(71) Applicant: RESMED PTY LTD, Bella Vista (AU)

(72) Inventors: Hargopal Verma, Sydney (AU); David Mulcahy, Sydney (AU); Michael James Dent, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 749 days.

(21) Appl. No.: 17/413,809

(22) PCT Filed: Dec. 17, 2019

(86) PCT No.: PCT/IB2019/060918
§ 371 (c)(1),
(2) Date: Jun. 14, 2021

(87) PCT Pub. No.: WO2020/128829
PCT Pub. Date: Jun. 25, 2020

(65) Prior Publication Data
US 2022/0016384 A1    Jan. 20, 2022

Related U.S. Application Data

(60) Provisional application No. 62/781,283, filed on Dec. 18, 2018.

(51) Int. Cl.
*A61M 16/16* (2006.01)
*A61M 16/00* (2006.01)
(Continued)

(52) U.S. Cl.
CPC .......... *A61M 16/16* (2013.01); *A61M 16/109* (2014.02); *A61M 2016/0027* (2013.01);
(Continued)

(58) Field of Classification Search
CPC .......... A61M 16/0066; A61M 16/0816; A61M 16/109; A61M 16/16; F24F 6/025; F24F 6/10
See application file for complete search history.

(56) References Cited

U.S. PATENT DOCUMENTS 141,175 A    7/1873    Shaw
366,022 A    7/1887    Palmer
(Continued)

FOREIGN PATENT DOCUMENTS

AU    2003265025 B2    4/2004
CA    2151992          6/1996
(Continued)

OTHER PUBLICATIONS

"Respiratory Physiology", by John B. West, Lippincott Williams & Wilkins, 9th edition published 2012 (8 pages).
(Continued)

*Primary Examiner* — Joseph D. Boecker
(74) *Attorney, Agent, or Firm* — Nixon & Vanderhye P.C.

(57) ABSTRACT

A water reservoir for an apparatus for humidifying a flow of breathable gas includes a reservoir body forming a cavity structured to hold a volume of liquid. The reservoir body comprises a conductive portion. The conductive portion comprises a thermally conductive material and is adapted to thermally engage with a heater plate to allow thermal transfer of heat to the liquid. The conductive portion includes a peripheral interfacing portion structured and arranged to connect the conductive portion to one or more walls of the reservoir body. The peripheral interfacing portion includes an intermediate portion and an end portion. The end portion is bent so as to be at least inclined with respect to the intermediate portion to reduce a risk of leakage caused by cracks within a critical area of a thickness of the
(Continued)

one or more walls due to a presence of a sharp edge at the end portion.

17 Claims, 17 Drawing Sheets

(51) Int. Cl.
    *A61M 16/10*     (2006.01)
    *A61M 16/06*     (2006.01)

(52) U.S. Cl.
    CPC ... *A61M 2016/003* (2013.01); *A61M 16/0066* (2013.01); *A61M 16/06* (2013.01); *A61M 16/161* (2014.02); *A61M 2205/3389* (2013.01)

(56) References Cited

U.S. PATENT DOCUMENTS

| | | |
|---|---|---|
| 1,192,357 A | 7/1916 | Thatcher |
| 2,023,324 A | 12/1935 | Johnson |
| 2,139,429 A | 12/1938 | Wilson |
| 2,266,705 A | 12/1941 | Coghlan |
| 3,414,117 A | 12/1968 | Leeds |
| 3,479,801 A | 11/1969 | Shohachiro |
| 3,617,698 A | 11/1971 | Duncanson |
| 3,936,026 A | 2/1976 | Hampel et al. |
| 4,203,027 A | 5/1980 | O'Hare et al. |
| 4,351,327 A | 9/1982 | Rinne |
| 4,782,832 A | 11/1988 | Trimble et al. |
| 4,836,401 A | 6/1989 | Ingemann |
| 4,921,642 A | 5/1990 | LaTorraca |
| 4,944,310 A | 7/1990 | Sullivan |
| 5,065,753 A | 11/1991 | Kalishman |
| 5,215,685 A | 6/1993 | Marino |
| 5,514,303 A | 5/1996 | Chiu |
| 5,529,060 A | 6/1996 | Salmon et al. |
| 5,558,084 A | 9/1996 | Daniell |
| 5,564,415 A | 10/1996 | Dobson et al. |
| 5,607,316 A | 3/1997 | Ishikawa |
| 5,701,950 A | 12/1997 | Imamura et al. |
| 5,704,345 A | 1/1998 | Berthon-Jones |
| 5,916,493 A | 6/1999 | Miller |
| 5,943,473 A | 8/1999 | Levine |
| 6,135,432 A | 10/2000 | Hebblewhite |
| 6,202,991 B1 | 3/2001 | Coniglio |
| 6,244,576 B1 | 6/2001 | Tsai |
| 6,256,454 B1 | 7/2001 | Dykes |
| 6,397,841 B1 | 6/2002 | Kenyon |
| 6,398,197 B1 | 6/2002 | Dickinson et al. |
| 6,532,959 B1 | 3/2003 | Berthon-Jones |
| 6,554,260 B1 | 4/2003 | Lipscombe |
| 6,581,594 B1 | 6/2003 | Drew et al. |
| 6,690,924 B1 | 2/2004 | Jan et al. |
| 6,918,389 B2 | 7/2005 | Seakins et al. |
| 6,935,337 B2 | 8/2005 | Virr |
| 7,096,864 B1 | 8/2006 | Mayer |
| 7,111,624 B2 | 9/2006 | Thudor et al. |
| 7,137,388 B2 | 11/2006 | Virr |
| 7,157,035 B2 | 1/2007 | Edirisuriya et al. |
| 7,393,222 B2 | 7/2008 | Asakura |
| 7,413,173 B2 | 8/2008 | DiMatteo et al. |
| 7,439,929 B2 | 10/2008 | Ozkar |
| 7,478,635 B2 | 1/2009 | Wixey et al. |
| 7,677,246 B2 | 3/2010 | Kepler et al. |
| 7,849,852 B2 | 12/2010 | Bremner |
| 7,866,944 B2 | 1/2011 | Kenyon et al. |
| 7,942,824 B1 | 5/2011 | Kayyali et al. |
| 8,006,691 B2 | 8/2011 | Kenyon et al. |
| 8,544,465 B2 | 10/2013 | Smith et al. |
| 8,545,416 B1 | 10/2013 | Kayyali et al. |
| 8,631,789 B2 | 1/2014 | Virr et al. |
| 8,636,002 B2 | 1/2014 | Mcauley et al. |
| 8,636,479 B2 | 1/2014 | Kenyon et al. |
| 8,638,014 B2 | 1/2014 | Sears et al. |
| 8,677,993 B2 | 3/2014 | Cortez, Jr. |
| 8,733,349 B2 | 5/2014 | Bath et al. |
| 8,770,432 B2 | 7/2014 | Rueckheim |
| 8,985,105 B2 | 3/2015 | Burton et al. |
| 10,342,950 B2 | 7/2019 | Bath et al. |
| 10,688,271 B2 | 6/2020 | Bath et al. |
| 10,864,343 B2 | 12/2020 | Bath et al. |
| 2001/0017134 A1 | 8/2001 | Bahr |
| 2001/0050080 A1 | 12/2001 | Seakins et al. |
| 2002/0014240 A1 | 2/2002 | Truschel |
| 2004/0017318 A1 | 1/2004 | Annabi et al. |
| 2005/0166921 A1 | 8/2005 | Devries et al. |
| 2005/0284475 A1 | 12/2005 | Loescher |
| 2006/0144405 A1 | 7/2006 | Gunaratnam et al. |
| 2006/0266365 A1 | 11/2006 | Stallard |
| 2007/0079826 A1 | 4/2007 | Kramer et al. |
| 2007/0132117 A1 | 6/2007 | Pujol |
| 2007/0193583 A1 | 8/2007 | Reed |
| 2007/0230927 A1 | 10/2007 | Kramer |
| 2007/0277827 A1 | 12/2007 | Bordewick et al. |
| 2008/0072900 A1 | 3/2008 | Lithgow et al. |
| 2008/0105257 A1 | 5/2008 | Klasek |
| 2008/0276939 A1 | 11/2008 | Tiedje |
| 2008/0302361 A1* | 12/2008 | Snow ............... A61M 16/109 128/202.27 |
| 2008/0316118 A1 | 12/2008 | Baliarda et al. |
| 2009/0000620 A1 | 1/2009 | Virr |
| 2009/0044808 A1 | 2/2009 | Guney et al. |
| 2009/0050156 A1 | 2/2009 | Ng et al. |
| 2009/0110378 A1 | 4/2009 | Bradley et al. |
| 2009/0120434 A1 | 5/2009 | Smith et al. |
| 2009/0152445 A1 | 6/2009 | Gardner |
| 2009/0156952 A1 | 6/2009 | Hunter et al. |
| 2009/0194106 A1 | 8/2009 | Smith et al. |
| 2010/0000534 A1 | 1/2010 | Kooij et al. |
| 2010/0154796 A1 | 6/2010 | Smith et al. |
| 2011/0017212 A1 | 1/2011 | Kenyon |
| 2011/0023874 A1 | 2/2011 | Bath et al. |
| 2011/0155132 A1 | 6/2011 | Virr et al. |
| 2011/0162649 A1 | 7/2011 | Potharaju et al. |
| 2011/0180068 A1 | 7/2011 | Kenyon et al. |
| 2011/0248082 A1 | 10/2011 | Treacy |
| 2011/0271956 A2 | 11/2011 | Smith et al. |
| 2011/0309992 A1 | 12/2011 | Ali |
| 2012/0012109 A1 | 1/2012 | Chalvignac |
| 2012/0146251 A1* | 6/2012 | Heine ............... A61M 16/1075 261/119.1 |
| 2012/0240932 A1 | 9/2012 | Gusky et al. |
| 2013/0008440 A1 | 1/2013 | Maurer et al. |
| 2013/0206140 A1 | 8/2013 | Kepler et al. |
| 2013/0269700 A1 | 10/2013 | Lapoint et al. |
| 2013/0310713 A1 | 11/2013 | Weber et al. |
| 2014/0264975 A1 | 9/2014 | Bath et al. |
| 2015/0202402 A1* | 7/2015 | Kat ............... A61M 16/0066 128/203.27 |
| 2016/0022954 A1 | 1/2016 | Bath et al. |
| 2016/0310691 A1 | 10/2016 | Bath et al. |
| 2018/0333556 A1* | 11/2018 | Ormrod ........... A61M 16/0051 |
| 2020/0306490 A1 | 10/2020 | Bath et al. |
| 2020/0316332 A1 | 10/2020 | Bath et al. |
| 2020/0398016 A1 | 12/2020 | Bath et al. |

FOREIGN PATENT DOCUMENTS

| | | |
|---|---|---|
| CN | 2327396 | 7/1999 |
| CN | 1691437 | 11/2005 |
| CN | 1829549 A | 9/2006 |
| CN | 101024105 A | 8/2007 |
| CN | 101052985 A | 10/2007 |
| CN | 201042552 Y | 4/2008 |
| CN | 101537221 A | 9/2009 |
| CN | 101541367 A | 9/2009 |
| CN | 101583395 A | 11/2009 |
| CN | 101678190 A | 3/2010 |
| CN | 201775525 U | 3/2011 |
| CN | 201823138 | 5/2011 |
| CN | 102170932 A | 8/2011 |
| CN | 201954697 U | 8/2011 |
| CN | 102686282 A | 9/2012 |
| CN | 102725015 A | 10/2012 |

(56) References Cited

FOREIGN PATENT DOCUMENTS

| | | |
|---|---|---|
| CN | 103055400 A | 4/2013 |
| CN | 103124575 A | 5/2013 |
| CN | 203183455 | 9/2013 |
| EP | 1 127 583 A2 | 8/2001 |
| EP | 1 369 141 A1 | 12/2003 |
| EP | 1 898 337 A1 | 3/2008 |
| EP | 1 900 387 A1 | 3/2008 |
| EP | 2 245 985 A1 | 11/2010 |
| EP | 2 471 568 A2 | 7/2012 |
| EP | 2 540 335 A1 | 1/2013 |
| EP | 2 703 034 A2 | 3/2014 |
| FR | 2579896 A1 | 10/1986 |
| GB | 1364127 A | 8/1974 |
| GB | 1 401 399 | 7/1975 |
| GB | 1 450 097 | 9/1976 |
| GB | 2 010 097 A | 6/1979 |
| JP | 48-23271 U | 7/1973 |
| JP | 59-55316 U | 4/1984 |
| JP | H03213293 | 9/1991 |
| JP | 5-312363 A | 11/1993 |
| JP | 7-55210 A | 3/1995 |
| JP | 10-76008 A | 3/1998 |
| JP | 10-137339 A | 5/1998 |
| JP | 2000-337670 A | 12/2000 |
| JP | 2001-274719 | 10/2001 |
| JP | 2004-188121 | 7/2004 |
| JP | 2005-27217 | 1/2005 |
| JP | 2005-538802 A | 12/2005 |
| JP | 2006-109534 A | 4/2006 |
| JP | 2009-504278 | 2/2009 |
| JP | 2009-508647 A | 3/2009 |
| JP | 2009-511218 | 3/2009 |
| JP | 2010-501315 | 1/2010 |
| JP | 2010-203626 A | 9/2010 |
| JP | 2011-005240 | 1/2011 |
| JP | 2011-525833 | 9/2011 |
| JP | 2012-502698 A | 2/2012 |
| JP | 2013-18017 A | 1/2013 |
| TW | 432746 | 5/2001 |
| TW | 200711671 A | 4/2007 |
| WO | WO 98/004310 A1 | 2/1998 |
| WO | WO 98/04311 A1 | 2/1998 |
| WO | WO 98/034665 A1 | 8/1998 |
| WO | WO 98/57691 A1 | 12/1998 |
| WO | WO 00/78381 | 12/2000 |
| WO | WO 2000/078381 A1 | 12/2000 |
| WO | WO 01/10489 A2 | 2/2001 |
| WO | WO 02/066107 A1 | 8/2002 |
| WO | WO 02/078775 A2 | 10/2002 |
| WO | 03/043560 A2 | 5/2003 |
| WO | WO 2004/026382 A1 | 4/2004 |
| WO | WO 2004/073778 A1 | 9/2004 |
| WO | WO 2004/112873 | 12/2004 |
| WO | 2005/063323 A1 | 7/2005 |
| WO | WO 2005/063328 A1 | 7/2005 |
| WO | WO 2006/074513 A1 | 7/2006 |
| WO | WO 2006/130903 A1 | 12/2006 |
| WO | WO 2006/138331 A1 | 12/2006 |
| WO | WO 2007/019625 | 2/2007 |
| WO | WO 2007/019626 A1 | 2/2007 |
| WO | WO 2007/038152 A2 | 4/2007 |
| WO | WO 2007/045017 A2 | 4/2007 |
| WO | WO 2007/051230 A1 | 5/2007 |
| WO | WO 2008/056993 A2 | 5/2008 |
| WO | WO 2008/148146 A1 | 12/2008 |
| WO | WO 2009/052560 A1 | 4/2009 |
| WO | WO 2009/156921 | 12/2009 |
| WO | WO 2010/031126 | 3/2010 |
| WO | WO 2010/135785 A1 | 12/2010 |
| WO | WO 2011/056080 | 5/2011 |
| WO | WO 2011/122964 A1 | 10/2011 |
| WO | WO 2011/149362 A1 | 12/2011 |
| WO | 2012/065999 A2 | 5/2012 |
| WO | 2012/095764 A1 | 7/2012 |
| WO | WO 2012/154064 A2 | 11/2012 |
| WO | WO 2012/160477 | 11/2012 |
| WO | WO 2012/171072 A1 | 12/2012 |
| WO | 2013/002650 | 1/2013 |
| WO | WO 2013/020167 A1 | 2/2013 |
| WO | 2013/135318 A1 | 9/2013 |
| WO | 2013/151447 A1 | 10/2013 |
| WO | 2013/163687 A1 | 11/2013 |
| WO | 2014/007655 A2 | 1/2014 |
| WO | WO 2014/025266 | 2/2014 |
| WO | 2014/038968 A1 | 3/2014 |
| WO | WO 2014/053010 A1 | 4/2014 |
| WO | 2014/138804 | 9/2014 |
| WO | 2014/205513 A1 | 12/2014 |

OTHER PUBLICATIONS

International Search Report issued in Application No. PCT/AU2014/000264, mailed May 13, 2014 (9 pages).
Written Opinion of the International Searching Authority issued in Application No. PCT/AU2014/000264, mailed May 13, 2014 (4 pages).
"CPAP System XT Series", Apex Medical Corp., published Aug. 2007, 4 pages.
International Preliminary Report on Patentability issued in PCT Application No. PCT/AU2014/000264 dated Sep. 15, 2015 (5 pages).
First Examination Report issued in corresponding New Zealand Application No. 631374 dated Oct. 29, 2015 (2 pages).
Patent Examination Report No. 1 issued in corresponding Australian Appln. No. 2014231714 dated Mar. 23, 2016 (2 pages).
Non-Final Office Action issued in related U.S. Appl. No. 14/211,346 dated Aug. 31, 2015 (25 pages).
First Office Action issued in corresponding Chinese Patent Application No. 201480028533.9 dated Jun. 30, 2016 with English language translation thereof (20 pages).
APEX XT-Auto Instruction Manual, USPTO to assume before Applicant's filing date (74 pages).
APEX "Introducing a new member of our CPAP family" APEX XT-AUTO, USPTO to assume before Applicant's filing date (2 pages).
Final Office Action issued in related U.S. Appl. No. 14/211,346 dated May 26, 2016 (23 pages).
Extended European Search Report issued in a corresponding European Application No. 14763136.0 dated Sep. 7, 2016.
Patent Examination Report No. 2 dated Oct. 19, 2016 issued in Australian Application No. 2014231714 (4 pages).
Office Action dated Mar. 1, 2017 issued in related U.S. Appl. No. 14/211,346 (27 pages).
First Examination Report dated Apr. 4, 2017 issued in New Zealand Application No. 730481 (2 pages).
Communication dated May 30, 2017 issued in European Application No. 14 763 136.0 (7 pages).
Office Action dated Oct. 2, 2017 issued in Taiwanese Application No. 103109227 with English translation (11 pages).
Notice of Reasons for Rejection dated Jan. 5, 2018 issued in Japanese Application No. 2015-561828 with English translation (11 pages).
Communication dated Jul. 16, 2018 issued in European Application No. 14763136.0 (8 pages).
Notice of Reasons for Rejection mailed Mar. 18, 2019 in Japanese Application No. 2018-111737, with English translation, 22 pages.
Second Examination Report dated Dec. 24, 2020 issued in New Zealand Application No. 760194 (4 pages)
Second Examination Report dated Dec. 23, 2020 issued in New Zealand Application No. 760195 (4 pages).
Second Examination Report dated Dec. 23, 2020 issued in New Zealand Application No. 760196 (4 pages).
Second Examination Report dated Jan. 22, 2021 issued in New Zealand Application No. 760189 (3 pages).
Office Action dated Feb. 22, 2021 issued in Chinese Application No. 201810846297.1 with English translation (11 pages).
Second Examination Report dated Feb. 24, 2021 issued in New Zealand Application No. 751047 (3 pages).

(56) References Cited

OTHER PUBLICATIONS

John Crane Type 6 Elastomer Bellows Seal, https://web.archive.org/web/20091229113803/http:/www.allsealsinc.com/johncrane/type6johncrane.pdf, captured Dec. 29, 2009, (4 pages).
Office Action dated Nov. 30, 2020 issued in Japanese Application No. 2019-010135 with English translation (10 pages).
First Examination Report dated Oct. 14, 2020 issued in New Zealand Application No. 760190 (5 pages).
First Examination Report dated Sep. 25, 2020 issued in New Zealand Application No. 760189 (4 pages).
First Examination Report dated Sep. 25, 2020 issued in New Zealand Application No. 760192 (4 pages).
First Examination Report dated Sep. 25, 2020 issued in New Zealand Application No. 760193 (4 pages).
Notification of the First Office Action dated Jul. 3, 2020 issued in Chinese Application No. 2018108462971 with English translation (19 pages).
First Examination Report dated Aug. 27, 2020 issued in New Zealand Application No. 766847 (3 pages).
First Examination Report dated Sep. 21, 2020 issued in New Zealand Application No. 760188 (7 pages).
First Examination Report dated Sep. 21, 2020 issued in New Zealand Application No. 760191 (3 pages).
First Examination Report dated Sep. 18, 2020 issued in New Zealand Application No. 760194 (4 pages).
First Examination Report dated Sep. 18, 2020 issued in New Zealand Application No. 760195 (4 pages).
First Examination Report dated Sep. 18, 2020 issued in New Zealand Application No. 760196 (4 pages).
Extended European Search Report dated Aug. 6, 2019 issued in European Application No. 19157258.5 (25 pages).
First Office Action issued in related Japanese Application No. 2016-540619, dated Oct. 29, 2018, with English translation (13 pages).
First Office Action issued in related Taiwanese Application No. 1031440004 dated Nov. 7, 2018, with English translation, (11 pages).
First Examination Report issued in New Zealand Application No. 749247 dated Jan. 18, 2019 (2 pages).
Notice of Opposition to Grant of Patent (Section 21) filed Jun. 27, 2016 by Fisher & Paykel Healthcare Limited in New Zealand Application No. 630762 (2 pages).
Statement of Case dated Aug. 26, 2016 filed by Fisher & Paykel Healthcare Limited in New Zealand Application No. 630762 (9 pages).
Amended Notice of Opposition to Grant of Patent (Section 21), with no markups, dated Aug. 26, 2016, filed by Fisher & Paykel Healthcare Limited in New Zealand Application No. 630762 (2 pages).
Amended Notice of Opposition to Grant of Patent (Section 21), with markups, dated Aug. 26, 2016, filed by Fisher & Paykel Healthcare Limited in New Zealand Application No. 630762 (2 pages).
Dolan, Brian, "Philips Respironics offers SleepMapper app to motivate, inform sleep apnea patients", Mobihealthnews, Apr. 25, 2013, (1 page).
HomeCare Magazine, "Connectivity Drives Compliance", Apr. 28, 2016, http://www.homecaremag.com/hmeproducts/connectivitydrivescompliance (8 pages).
Second Amended Notice of Opposition to Grant of Patent (Section 21), with no markups, dated Nov. 22, 2016, filed by Fisher & Paykel Healthcare Limited in New Zealand Application No. 630762 (2 pages).
Second Amended Notice of Opposition to Grant of Patent (Section 21), with markups, dated Nov. 22, 2016, filed by Fisher & Paykel Healthcare Limited in New Zealand Application No. 630762 (2 pages).
Amended Statement of Case, with no markups, dated Nov. 21, 2016 filed by Fisher & Paykel Healthcare Limited in New Zealand Application No. 630762 (10 pages).
Amended Statement of Case, with markups, dated Nov. 21, 2016 filed by Fisher & Paykel Healthcare Limited in New Zealand Application No. 630762 (11 pages).
Second Amended Statement of Case, with no markups, dated Jan. 25, 2017 filed by Fisher & Paykel Healthcare Limited in New Zealand Application No. 630762 (10 pages).
Second Amended Statement of Case, with markups, dated Jan. 25, 2017 filed by Fisher & Paykel Healthcare Limited in New Zealand Application No. 630762 (10 pages).
Third Amended Notice of Opposition to Grant of Patent (Section 21), with no markups, filed Feb. 7, 2018 by Fisher & Paykel Healthcare Limited in New Zealand Application No. 630762 (2 pages).
Third Amended Notice of Opposition to Grant of Patent (Section 21). with markups, filed Feb. 7, 2018 by Fisher & Paykel Healthcare Limited in New Zealand Application No. 630762 (2 pages).
Third Amended Statement of Case, with no markups, dated Feb. 7, 2018 filed by Fisher & Paykel Healthcare Limited in New Zealand Application No. 630762 (13 pages).
Third Amended Statement of Case, with markups, dated Feb. 7, 2018 filed by Fisher & Paykel Healthcare Limited in New Zealand Application No. 630762 (13 pages).
Xu, Lie Jie, and Guo, Yong-Xin, "Dual-Band Implantable Antenna with Open-End Slots on Ground", IEEE Antennas and Wireless Propagation Letters, vol. 11, 2012, pp. 1564-1567 (4 pages).
First Office Action issued in Taiwanese Application No. 103121801 dated Jun. 20, 2018 with English translation (7 pages).
Extended European Search Report issued in European Application No. 18 16 7630.5 dated Jun. 20, 2018, (10 pages).
First Office Action issued in related Japanese Application No. 2016-522136 dated May 14, 2018, with English translation, 8 pages.
First Office Action issued in Chinese Application No. 201480075670.8 dated Mar. 12, 2018, with English translation, 11 pages.
Extended European Search Report issued in related European Application No. 14871575.8 dated Sep. 20, 2017, (16 pages).
Kin-Lu Wong, *Compact and Broadband Microstrip Antennas*, (2002) (340 pages).
First Office Action issued in related Chinese Application No. 201480046956.3 with English translation, dated Mar. 28, 2017, 15 pages.
Extended Search Report issued in related European Application No. 14818607.5, dated Nov. 15, 2016, 8 pages.
International Preliminary Report on Patentability for PCT/AU2014/050426 mailed Jun. 21, 2016, 8 pages.
International Search Report for PCT/AU2014/050089, mailed Oct. 1, 2014, 12 pages.
Written Opinion of the ISA for PCT/AU2014/050089, mailed May 28, 2015, 6 pages.
Written Opinion of the ISA for PCT/AU2014/050089, mailed Oct. 1, 2014, 7 pages.
International Preliminary Report on Patentability for PCT/AU2014/050089, Jun. 15, 2015, 50 pages.
"BalContact Springs Current Carrying Contact Elements DM-7, BalContact Advantages", BAL SEAL Canted Coil Spring Catalog, Report No. 621-9, 2003, Bal Seal Engineering Company, Inc., 27 pages.
Patent Examination Report No. 1 issued in related Australian Application No. 2014301955, dated Feb. 16, 2016, 2 pages.
First Examination Report issued in related New Zealand Application No. 631008, dated Feb. 18, 2016, 2 pages.
Written Opinion for PCT/AU2014/050426 mailed Mar. 16, 2015, 7 pages.
International Search Report for PCT/AU2014/050426 mailed Mar. 16, 2015, 8 pages.
Notice of Reasons for Rejection dated Jan. 20, 2020 issued in Japanese Application No. 2019-010135 with English translation (16 pages).
Extended European Search Report dated Aug. 9, 2022 issued in European Application No. 19899859.3 (11 pages).
Extended European Search Report dated Sep. 17, 2024 issued in European Application No. 24182769.0 (10 pages).

* cited by examiner

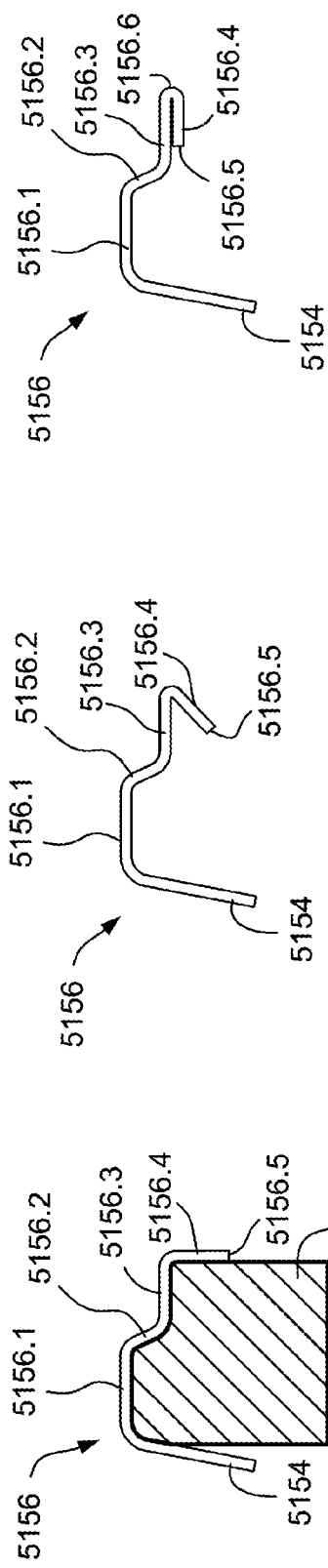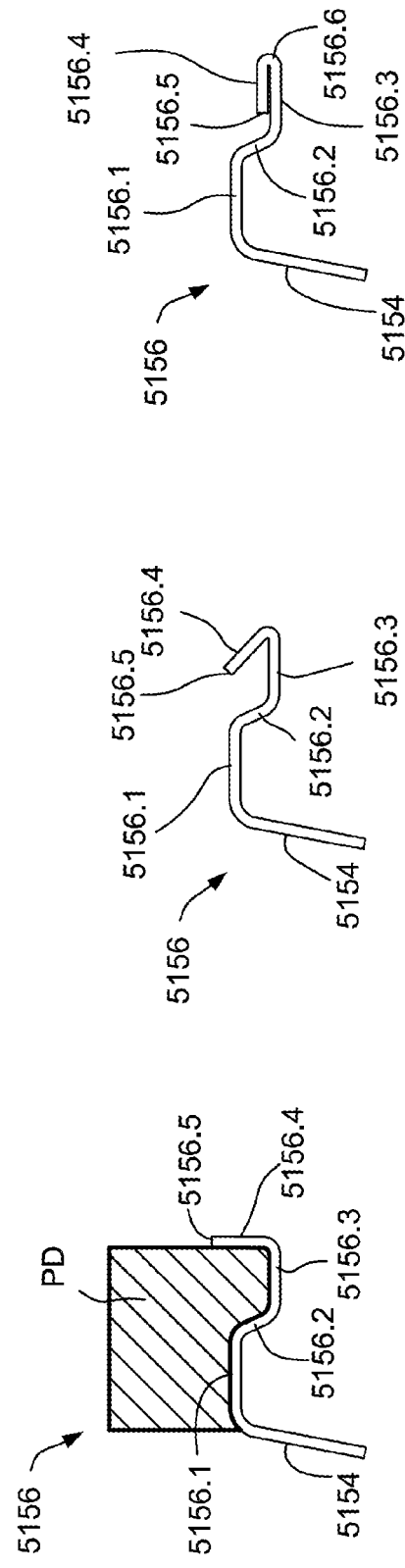

HUMIDIFIER RESERVOIR

1 CROSS-REFERENCE TO RELATED APPLICATIONS

This application is the U.S. national phase of International Application No. PCT/IB2019/060918 filed Dec. 17, 2019 which designated the U.S. and claims priority to U.S. Provisional Application No. 62/781,283 filed Dec. 18, 2018, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or where a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB (A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology relates to a CPAP system including a humidifier, a patient interface, and an air delivery tube to deliver humidified air to the patient interface. In an example, the humidifier is integrated with an RPT device structured to produce a flow of air at positive pressure.

Another aspect of the present technology relates to a humidifier including a water reservoir including a cavity structured to hold a volume of water, and a water reservoir dock structured and arranged to receive the water reservoir in an operative position.

Another aspect of the present technology relates to a water reservoir including a cavity structured to hold a volume of water, the water reservoir comprising a conductive portion to allow thermal transfer of heat to the volume of liquid.

Another aspect of the present technology relates to a water reservoir for an apparatus for humidifying a flow of breathable gas. The water reservoir, which may throughout this specification also be referred as a reservoir, a humidification reservoir or a humidification tub, includes a reservoir body forming a cavity structured to hold a volume of liquid. The reservoir body comprises a conductive portion provided at a lower portion of the reservoir body. The conductive portion comprises a thermally conductive material and is adapted to thermally engage with a heater plate to allow thermal transfer of heat from the heater plate to the volume of liquid. The conductive portion is usually made of metal and it can also be referred to as a "metal conductive portion". The conductive portion may also be made of other non-metallic thermo-conductive materials. The conductive portion includes a peripheral interfacing portion structured and arranged to connect the conductive portion to one or more walls of the reservoir body. The peripheral interfacing portion includes an intermediate portion and an end portion, and the end portion is bent so as to be at least inclined with respect to the intermediate portion to reduce a risk of leakage caused by cracks within a critical area of a thickness of the one or more walls due to a presence of a sharp edge at the end portion.

Another aspect of the present technology relates to a water reservoir for an apparatus for humidifying a flow of breathable gas. The water reservoir includes a reservoir body forming a cavity structured to hold a volume of liquid. The reservoir body comprises a conductive portion provided at a lower portion of the reservoir body. The conductive portion comprises a thermally conductive material and is adapted to thermally engage with a heater plate to allow thermal transfer of heat from the heater plate to the volume of liquid. The conductive portion includes a peripheral interfacing portion structured and arranged to connect the conductive portion to one or more walls of the reservoir body. The conductive portion includes a sealing material provided to at least a portion of the peripheral interfacing portion. The one or more walls of the reservoir body comprises an overmolded connection to the peripheral interfacing portion and the sealing material thereof. In an example, the sealing material may comprise a silicone material. In an example, the silicone material may be overmolded or dispensed as a bead along at least a portion of the peripheral interfacing portion.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Patient Interface

FIG. 2 shows a patient interface in the form of a nasal mask in accordance with one form of the present technology.

4.3 RPT Device

FIG. 3 shows an RPT device in accordance with one form of the present technology.

4.4 Humidifier

FIGS. 8A to 8C show a method for bending a metal conductive portion according to an example of present technology.

FIGS. 9A to 9C show a method for bending a metal conductive portion according to another example of present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 TREATMENT SYSTEMS

Figure 1:
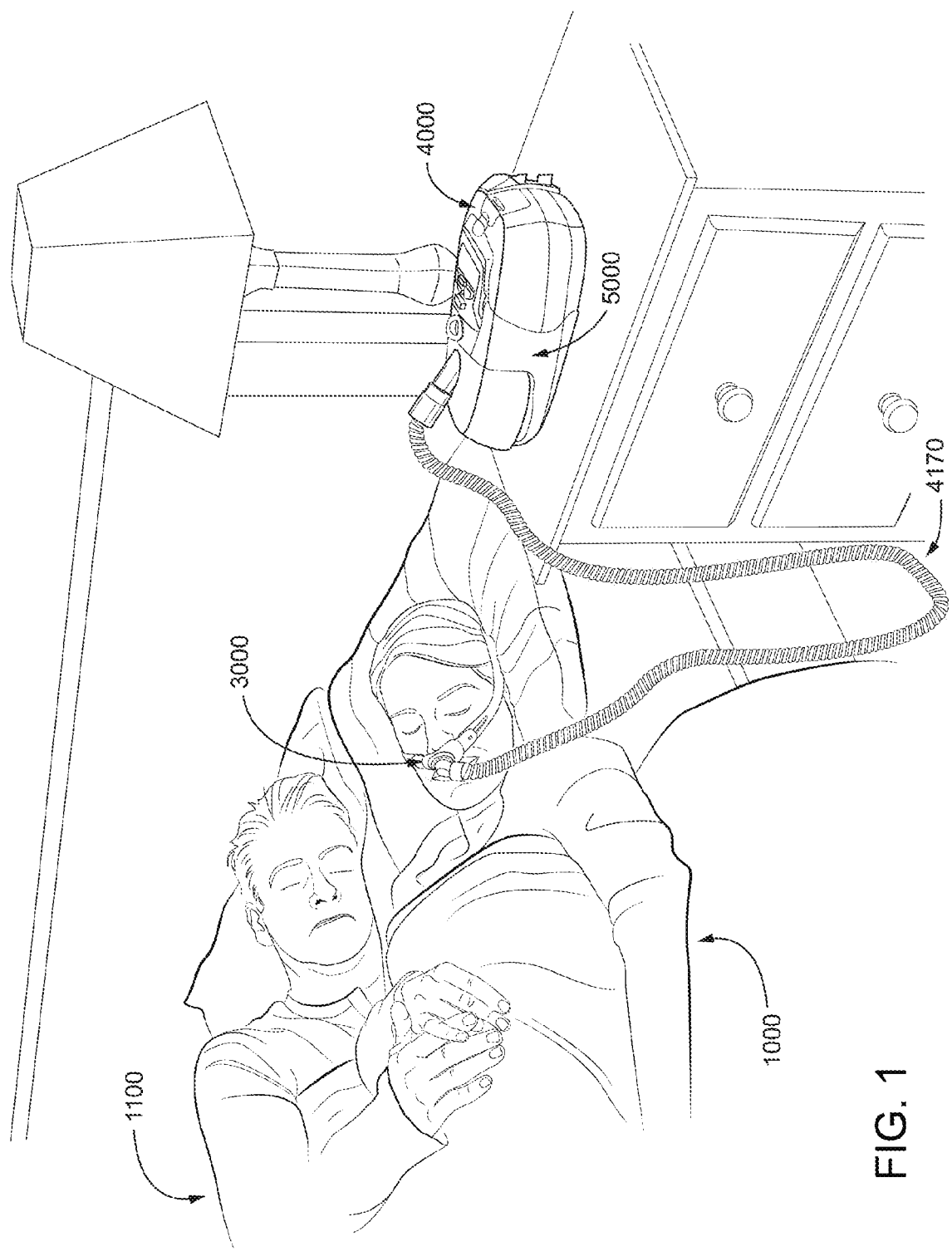

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIG. 1.

5.3 PATIENT INTERFACE

Figure 2:
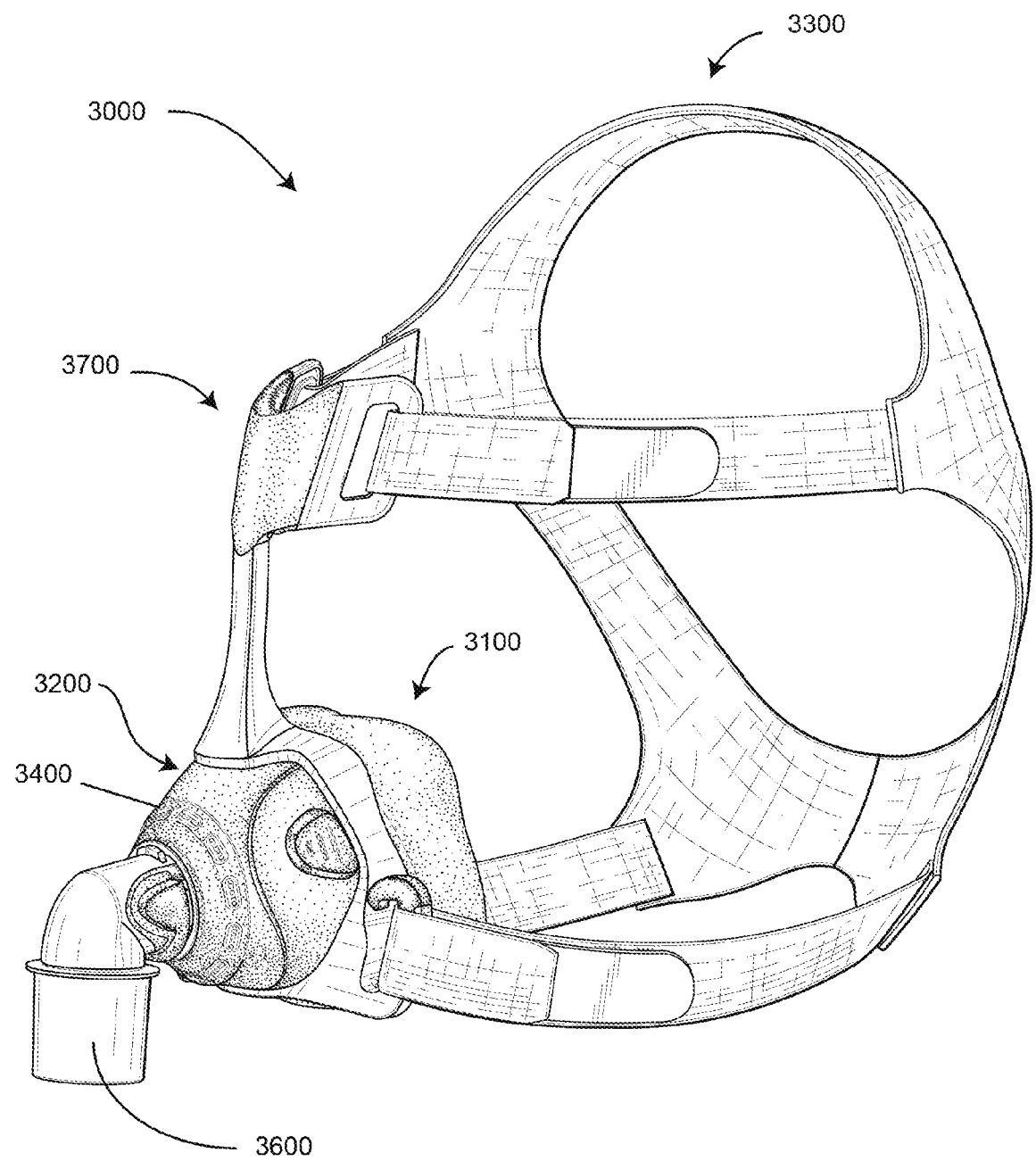

As shown in FIG. 2, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT DEVICE

Figure 3:
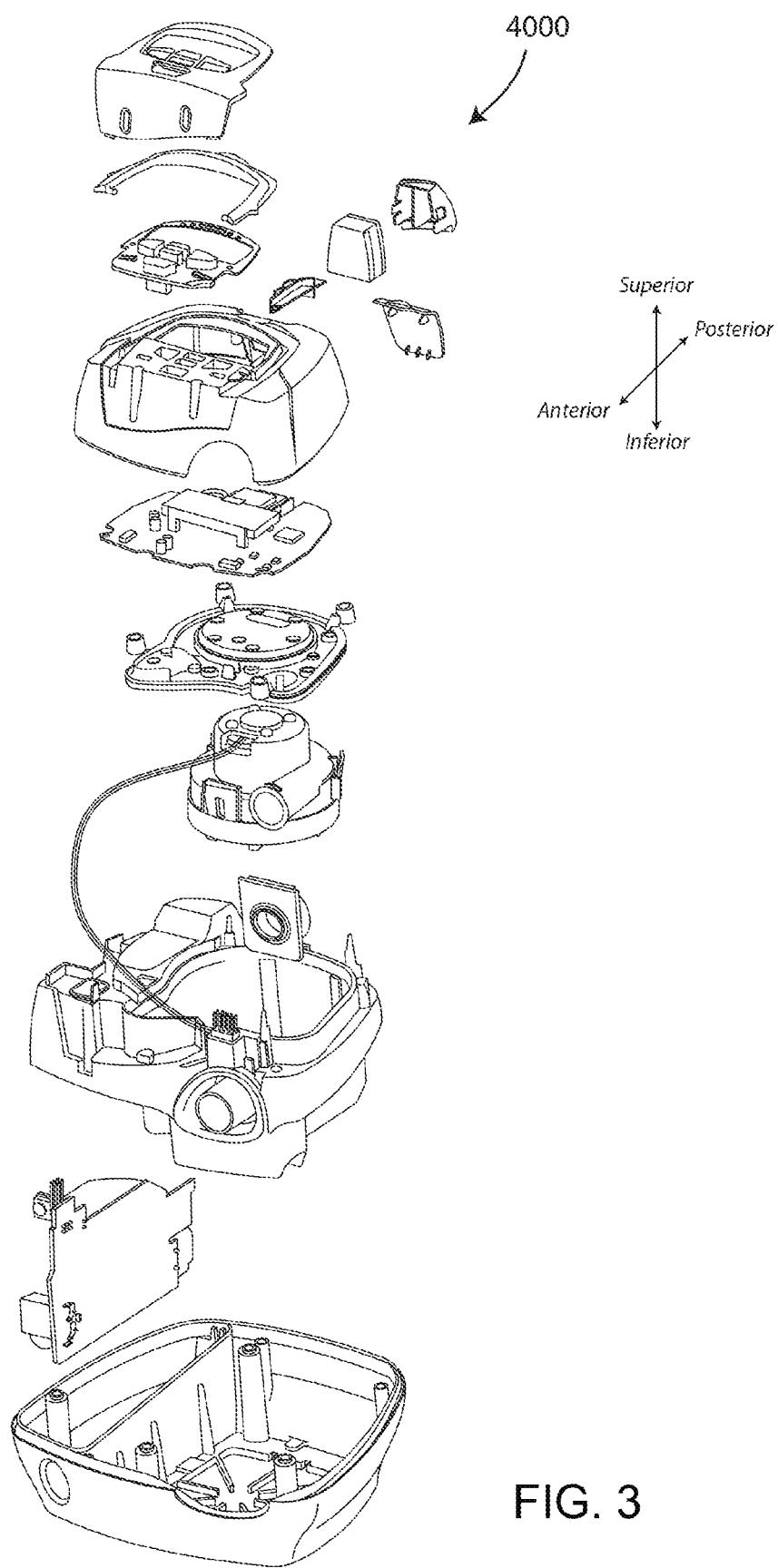

An RPT device 4000 in accordance with one aspect of the present technology comprises mechanical, pneumatic, and/or electrical components, e.g., see FIG. 3, and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

A power supply may be located internal or external of the external housing of the RPT device 4000.

In one form of the present technology, power supply provides electrical power to the RPT device 4000 only. In another form of the present technology, power supply provides electrical power to both RPT device 4000 and humidifier 5000.

In one form of the present technology, the RPT device includes a central controller including one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers, one or more input devices, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.6 HUMIDIFIER

5.6.1 Humidifier Overview

In one form of the present technology there is provided a humidifier to change the absolute humidity of air or gas for delivery to a patient relative to ambient air. Typically, the humidifier is used to increase the absolute humidity and increase the temperature of the flow of air (relative to ambient air) before delivery to the patient's airways.

Figure 4A:
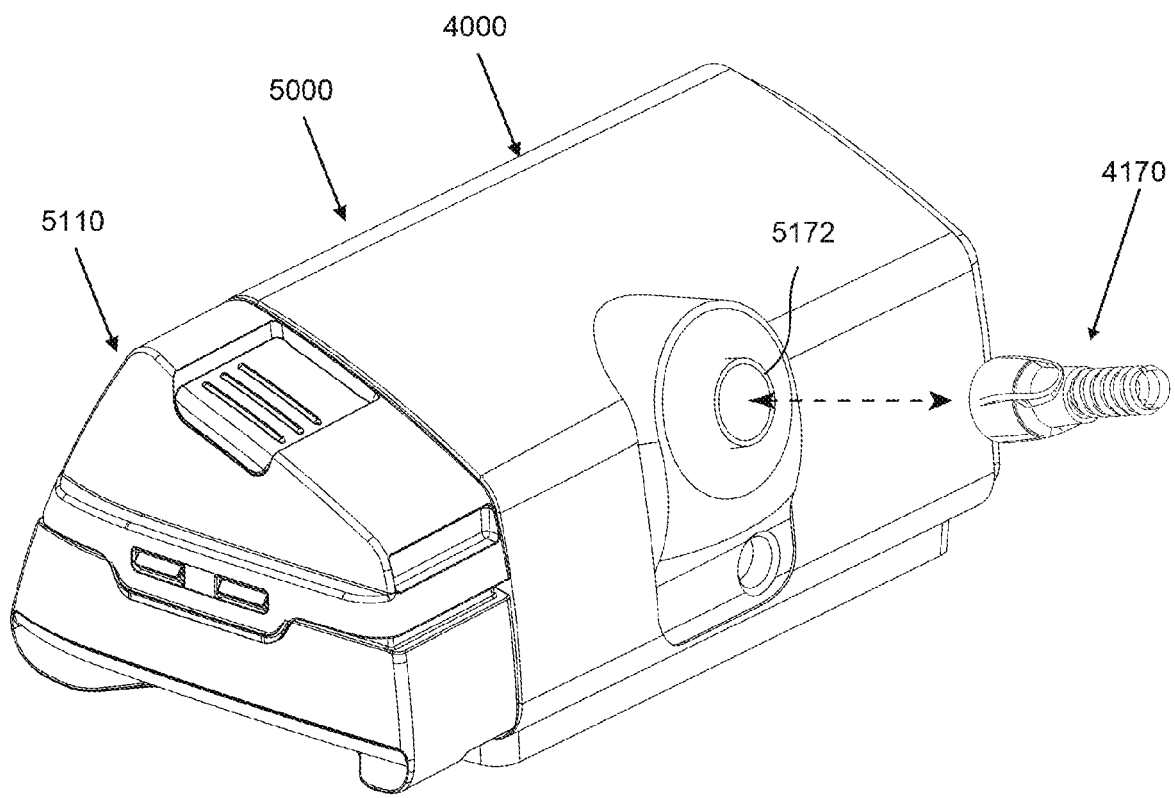
FIG. 4A is a perspective view of an RPT device and an integrated humidifier according to an example of the present technology, and demonstrating engagement of the humidifier with the air circuit according to an example of the present technology.
Figure 4B:
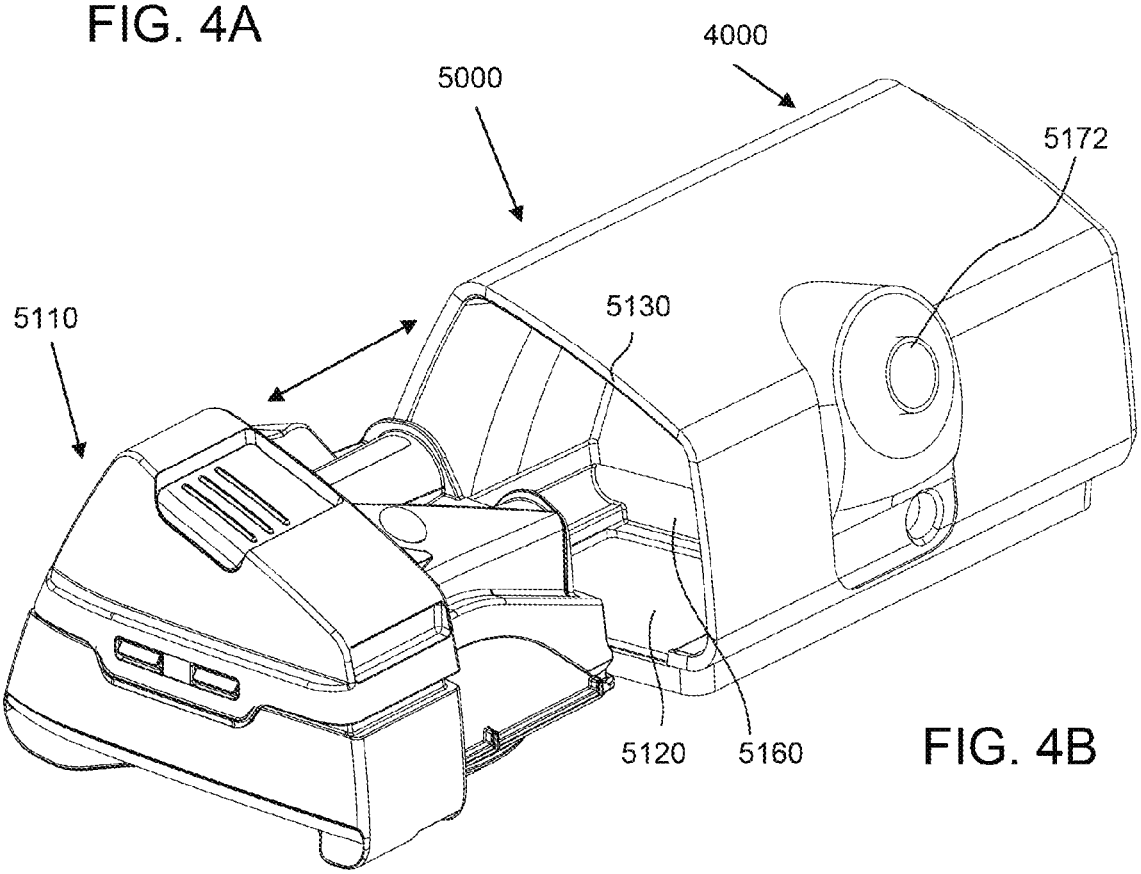
FIG. 4B is a perspective view of the RPT device and integrated humidifier of FIG. 4A demonstrating engagement of the humidifier reservoir with the reservoir dock according to an example of the present technology.
Figure 4C:
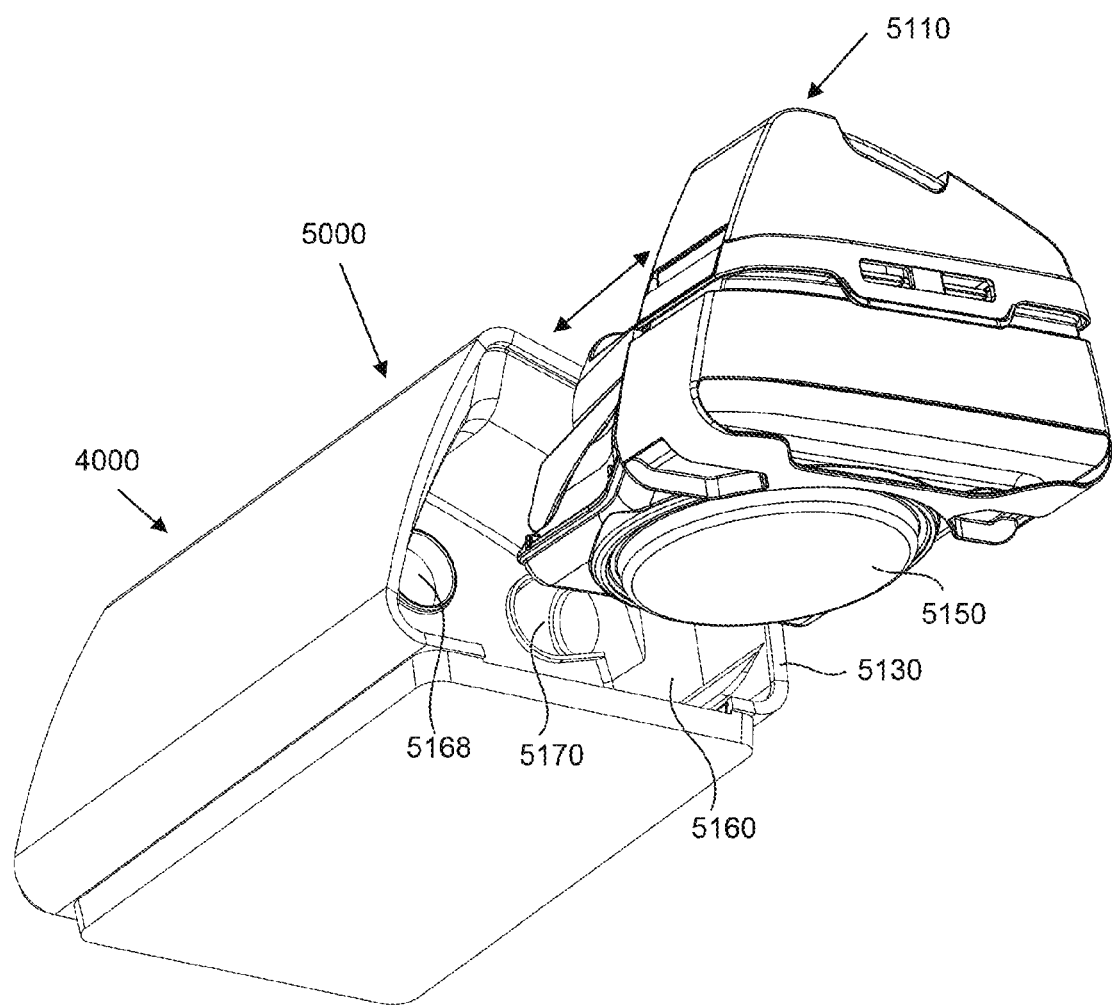
FIG. 4C is another perspective view of the RPT device and integrated humidifier of FIG. 4A demonstrating engagement of the humidifier reservoir with the reservoir dock according to an example of the present technology.

FIGS. 4A to 4C show a RPT device 4000 and an integrated humidifier 5000 according to an example of the present technology. In the illustrated example, the humidifier 5000 includes a water reservoir dock 5130 structured to receive a water reservoir 5110. Water reservoir 5110 may, throughout this specification, also be referred as a reservoir, a humidification reservoir or a humidification tub. As shown in FIGS. 4A to 4C, the water reservoir dock 5130 includes a cavity 5160 formed therein to receive the water reservoir 5110, e.g., the water reservoir 5110 may be insertable/removable from the water reservoir dock 5110 in a lateral direction.

In the illustrated example, the RPT device 4000 is integrated with the humidifier 5000. In this arrangement, the water reservoir dock 5130 is structured to connect the water reservoir 5110 to the pneumatic path. As best shown in FIGS. 4A and 4C, the reservoir dock 5130 comprises a dock air outlet 5168 to deliver a flow of air to the water reservoir 5110, a dock air inlet 5170 to receive the flow of air that has been humidified in the water reservoir 5110, and a humidifier outlet 5172 to transfer the flow of humidified air to the air circuit 4170. The cavity 5160 may include a top portion configured to cover at least a portion of the lid of the water reservoir 5110 and a bottom portion including a heater plate 5120.

However, it should be appreciated that the reservoir dock 5130 may be provided separately to RPT device 4000 in an alternative arrangement. In such an arrangement, additional interfaces may be used to connect the reservoir dock 5130 to the RPT device 4000, e.g., directly coupled or coupled via an air circuit.

In another arrangement, the water reservoir dock 5130 may comprise an opening in a substantially horizontal plane, so that the water reservoir 5110 may be inserted from above or below the water reservoir dock 5130.

Further examples and details of such RPT device 4000 and integrated humidifier 5000 are described in PCT Publication No. WO 2014/138804, published Sep. 18, 2014, which is incorporated herein by reference in its entirety.

5.6.2 Humidifier Components 5.6.2.1 Water Reservoir

Figure 5A:
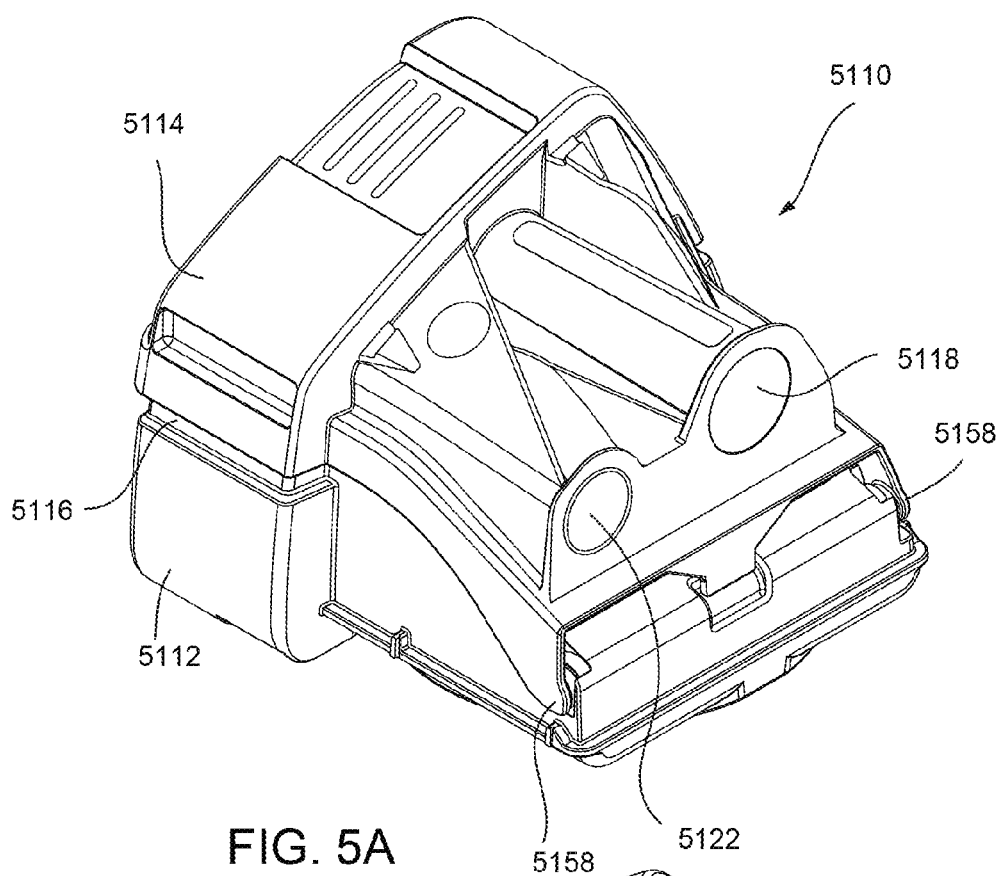
FIGS. 5A and 5B show top and bottom perspective views of a humidifier reservoir according to an example of present technology.
Figure 5B:
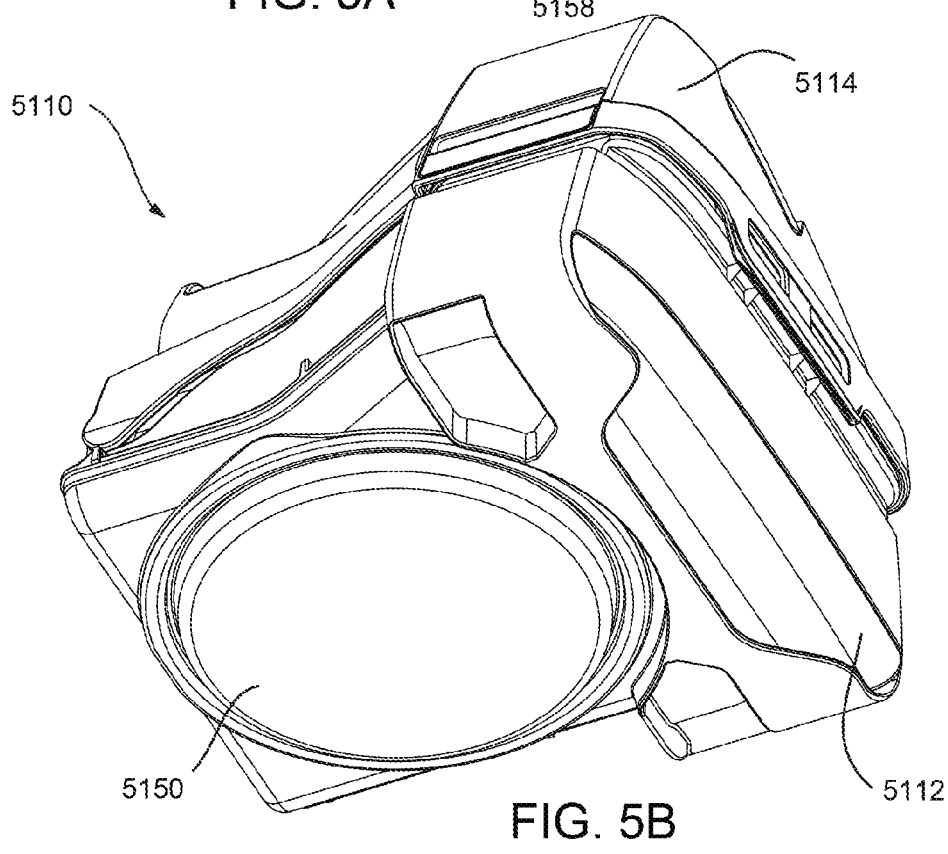

FIGS. 5A and 5B show a water reservoir or tub 5110 according to an example of the present technology. The water reservoir 5110 includes a cavity (e.g., provided by a body or base of the water reservoir) configured to hold, or retain, a volume of liquid (e.g., water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml, although it is to be understood that other volumes of liquid may be utilized, e.g., at least 100 ml. In other forms, the humidifier 5000 may be configured to receive a supply of water from an external water source such as a building's water supply system.

In the illustrated example, the water reservoir 5110 includes a reservoir body or base 5112 and a reservoir lid 5114 removably coupled to the reservoir base. A compliant portion or deformable seal 5116 may be provided to the reservoir lid 5114 and/or to the reservoir base 5112. When the reservoir lid 5114 is coupled to the reservoir base 5112, the seal 5116 is structured and arranged to engage between the reservoir lid 5114 and the reservoir base 5112 to seal the reservoir lid 5114 and the reservoir base 5112 and prevent egress of water from the water reservoir 5110. The reservoir lid 5114 may be structured to be fully removable from the reservoir base 5112, e.g., for patient usability to clean the interior of the reservoir base 5112 and/or the reservoir lid 5114. In an alternative example, the reservoir lid 5114 may be permanently attached to the reservoir base 5112.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the water reservoir 5110 may be removable from the humidifier 5000, for example in a lateral direction as shown in FIG. 4B and FIG. 4C.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

In the illustrated example, the reservoir lid 5114 comprises an inlet 5118 for receiving the flow of air into the reservoir 5110 and an outlet 5122 for delivering a flow of air from the reservoir 5110. The reservoir lid 5114 is pivotably connected to the base 5112 by hinges 5158 to allow the reservoir 5110 to be converted between a closed configuration, as shown in FIGS. 5A and 5B, and an open configuration. When the water reservoir 5110 is in its closed configuration, the compliant portion 5116 is put into sealing engagement between the base 5112 and the lid 5114 to seal the base 5112 and the lid 5114 and prevent egress of water from the reservoir 5110. The compliant portion 5116 may also perform other functions, such as to improve thermal contact between the reservoir 5110 and the heater plate 5120.

The reservoir base 5112 may be configured as a receptacle to retain the given, maximum volume of liquid that the reservoir 5110 is configured to hold. In one form, the base 5112 may comprise further features such as an overfill prevention feature, e.g., at least one orifice 5138 in the water reservoir 5110 to indicate over-filling as shown in FIG. 7A.

Figure 7A:
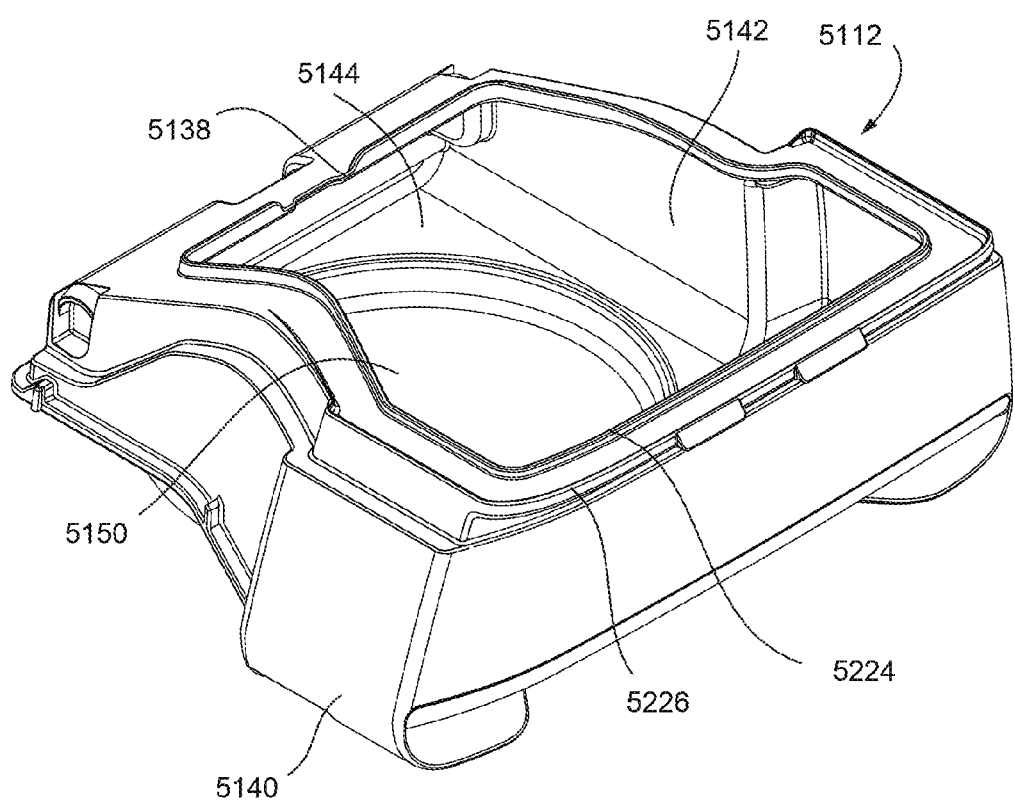
FIG. 7A is a top perspective view of a reservoir base of a humidifier reservoir according to an example of present technology.

In one form, the reservoir base 5112 may further comprise an inner lip 5224 and/or an outer lip 5226, for example as shown in FIG. 7A. According to one aspect, the inner lip 5224 and/or outer lip 5226 may prevent egress of liquid from the reservoir 5110 through the interface between an intermediate portion (e.g., the compliant portion 5116) and the base 5112, for example when the intermediate portion is compressed, or when the intermediate portion is under vibration.

In one form, the reservoir base 5112 includes a main body 5140 and a conducive portion 5150 which together form a receptacle. However, it should be appreciated that the reservoir base 5112 may be constructed in other number of parts.

In an example, the main body 5140 and/or the lid 5114 may be constructed from a bio-compatible material suitable for retaining the volume of liquid, such as a plastic or thermoplastic polymer material, for example, acrylonitrile butadiene styrene (ABS) or polycarbonate or copolyester materials. However, it should be appreciated that the main body 5140 and/or lid 5114 may comprise other suitable materials.

Further examples of the water reservoir are described in PCT Publication No. WO 2014/138804, published Sep. 18, 2014, which is incorporated herein by reference in its entirety.

5.6.2.2 Conductive Portion

According to one arrangement, the reservoir 5110 comprises a conductive portion 5150 configured to allow efficient transfer of heat from the heater plate 5120 to the volume of liquid in the reservoir 5110. The conductive portion 5150 comprises a heat conducting material structured and arranged for thermal engagement or contact with the heater plate 5120 so as to allow thermal transfer of heat from the heater plate 5120 to the volume of liquid. In one form, the conductive portion may be arranged as a circular plate, although other shapes may also be suitable. All or a part of the conductive portion may be made of a thermally conductive metal sheet such as aluminium, stainless steel sheet, (e.g. approximately 2 mm thick, such as 0.2 mm, 0.3 mm, 0.4 mm, 1 mm, 1.5 mm, 2.5 mm or 3 mm), or any other heat conducting material, including heat conductive plastics. In some cases, suitable heat conductivity may be achieved with less conductive materials of suitable geometry.

Figure 6A:
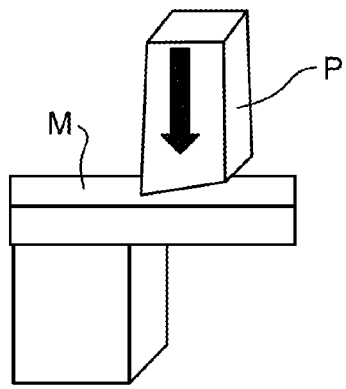
FIG. 6A to 6C are sequential schematic views of a blanking process of a metal sheet.
Figure 6B:
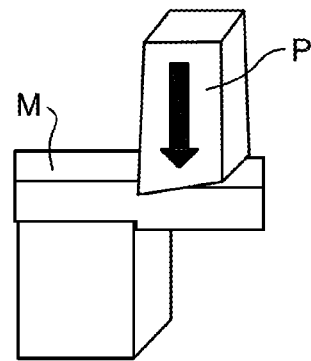
Figure 6C:
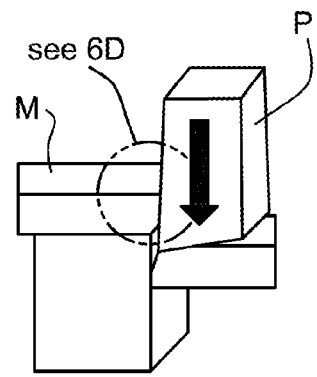

FIGS. 6A to 6C are sequential schematic views of an exemplary blanking process known in the art, e.g., for cutting sheet metal M into a desired shape, a process that can optionally be used for forming the metal conductive portion

Figure 6D:
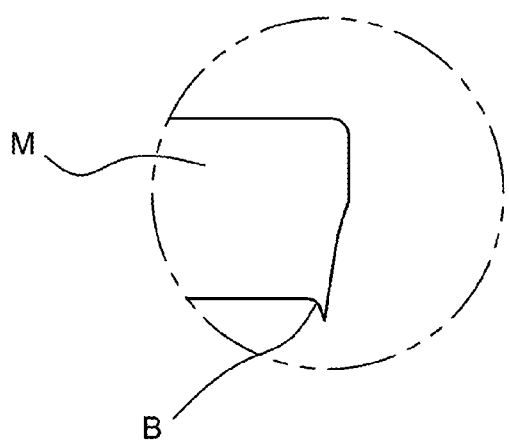
FIG. 6D is an enlarged view of a portion of the metal sheet's edge, after the blanking process of FIG. 6C showing burr formation in sheet metal.

5150. As illustrated, sheet metal M may be sheared by a punch P to form a blank or desired shape. As shown in FIG. 6D, the blanking process for sheet metal may create a sharp edge or burr B on a side of the blank. Any sharp edge or burr, once integrated into plastic molding, is a source of stress concentration and during the life of a product it can propagate a crack in the plastic molding. In the context of a water reservoir, any crack is a risk of water leak.

Figure 6E:
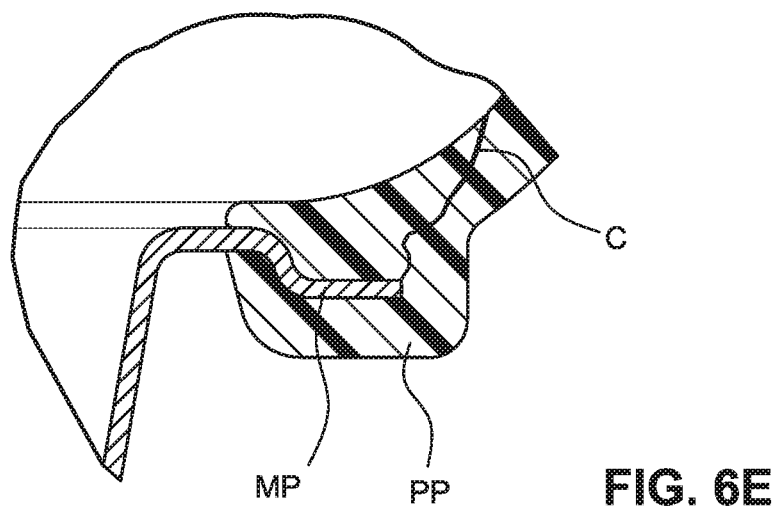
FIG. 6E is a cross-sectional view showing a possibility of crack propagation in a reservoir's wall due to a burr.
Figure 6F:
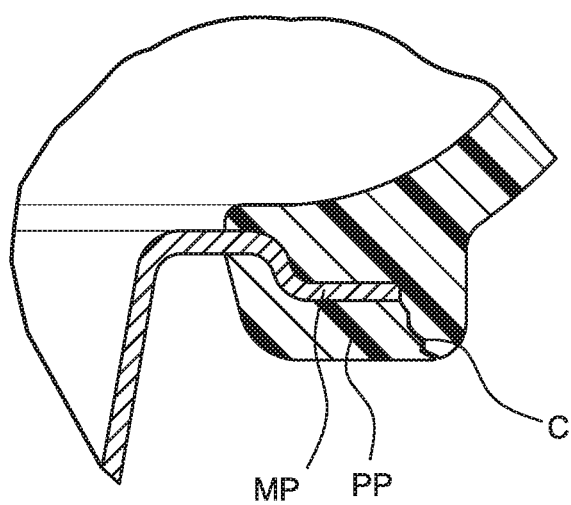
FIG. 6F is a cross-sectional view showing another possibility of crack propagation in a reservoir's wall due to a burr.

For example, FIG. 6E is a cross-sectional view showing a possibility of crack propagation C within a plastic material portion PP due to the sharp edge or burr of a metal plate MP. The burr in this case is formed on the edge of the upper side of the metal conductive portion 5150. The risk of stress concentration still exists if the blanking process was modified to change the burr side, e.g., see FIG. 6F showing another possibility of crack propagation C within a plastic material portion PP due to the sharp edge or burr of a metal plate MP, the burr this time being created on the edge of the lower side of metal conductive portion 5150, facing the heater plate 5120.

To remove this sharp edge or burr from a metal plate, a secondary process may be used, e.g., such as Electro polishing (chemical process) or linishing (mechanical process), etc. However, such secondary process may increase manufacturing cost and time, and may not sufficiently remove the source of stress concentration.

An aspect of the present technology relates to a metal conductive portion 5150 that is structured and arranged to reduce or eliminate stress concentration at the interface between the metal conductive portion 5150 and the plastic material main body 5140, thereby reducing or eliminating the possibility of crack propagation within the plastic material main body 5140 during the life of the reservoir base 5112.

FIGS. 7A to 7D show the reservoir base 5112 according to an example of the present technology. In the illustrated example, the reservoir base 5112 comprises two-part construction, i.e., only a main body 5140 and a conductive portion 5150. It should be noted that the described technology refers mostly to the conductive portion 5150 which is applicable to a variety of water reservoir structures. For example, in the illustrated examples, the water reservoir 5110 includes a reservoir body or base 5112 and a reservoir lid 5114 removable coupled to the reservoir base 5112. However, the described technology is equally applicable to reservoir structures where the reservoir lid is not openable/removable and is permanently attached to the reservoir base, to form an integral reservoir body.

In the illustrated example, the main body 5140 comprises a plurality of walls and the conductive portion 5150 is provided to a bottom one of the walls to form a chamber or cavity to hold the volume of water. For example, the main body 5140 includes side walls 5142 extending around the perimeter of the main body 5140 and a bottom wall 5144 that joins the side walls 5142. The conductive portion 5150 is provided or otherwise incorporated into the bottom wall 5144, forming part of the chamber for holding water. For example, the bottom wall 5144 includes a hole structured to receive the conductive portion 5150. The conductive portion 5150 is sealingly secured within the hole in an operative position so as to form at least a portion of a bottom of the reservoir base 5112.

In an example, the conductive portion 5150 is provided as a separate and distinct structure from the main body 5140 and then secured or otherwise provided to the bottom wall 5144 in an operative position, e.g., the conductive portion 5150 comprises a pre-formed structure that is secured to the bottom wall 5144.

In an example, the conductive portion 5150 comprises a metallic material, e.g., metal plate, and the main body 5140 comprises a plastic or thermoplastic polymer material.

In an example, the metal conductive portion 5150 may be pre-formed, and then insert molded to the plastic material main body 5140. For example, the metal conductive portion 5150 is first formed into its working configuration by one or more metal-forming processes. The metal conductive portion 5150 or insert is then inserted into an injection mold for the main body 5140 prior to melt injection. During the injection process, the melt flows around the edges of the metal conductive portion 5150 and locks or connects the metal conductive portion 5150 to the main body 5140 as the melt solidifies. The surfaces of metal conductive portion 5150 or insert may be chemically treated or Plasma treated before being inserted into the injection mold to enhance the bonding between metal and plastic.

Figure 7B:
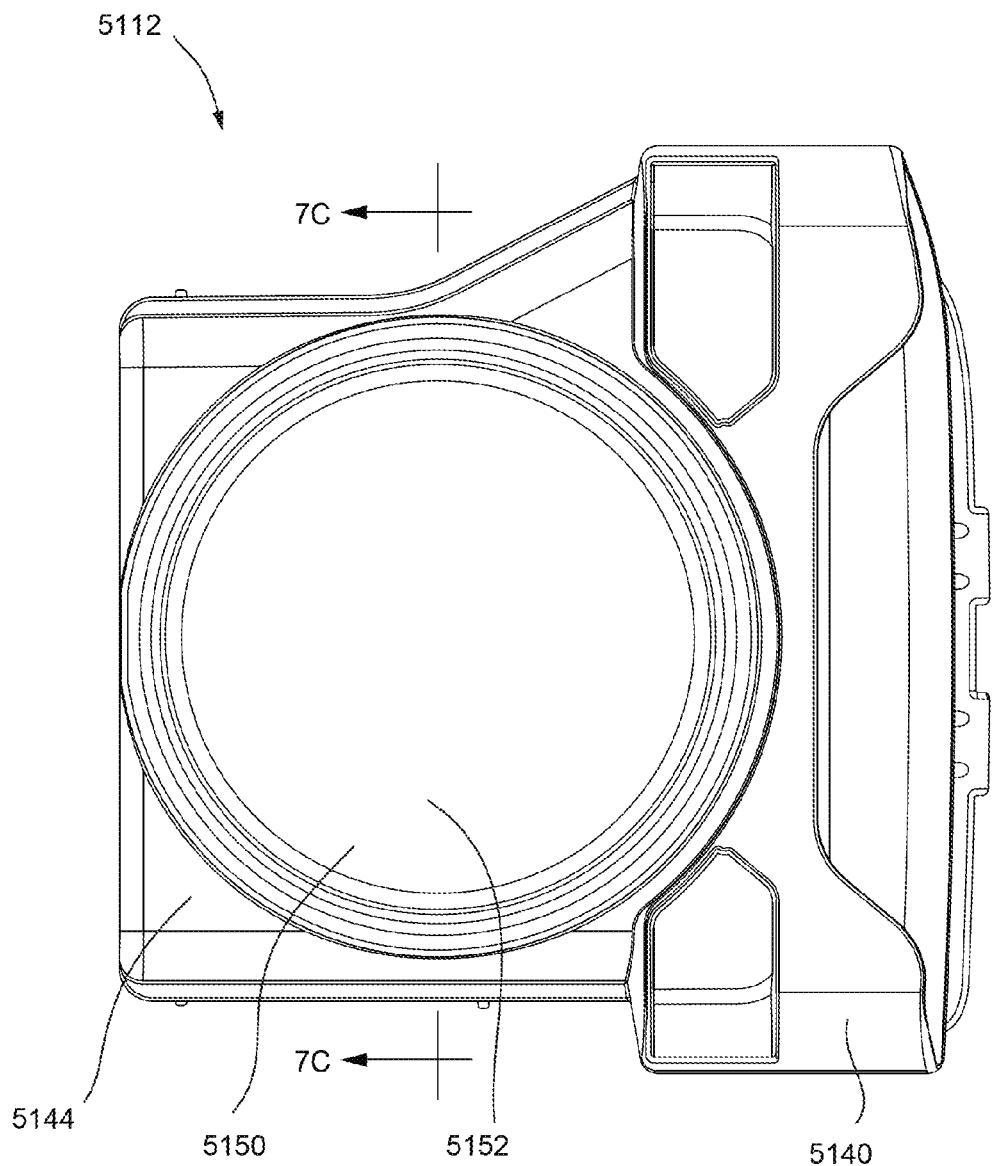
FIG. 7B is a bottom view of the reservoir base of FIG. 7A.
Figure 7C:
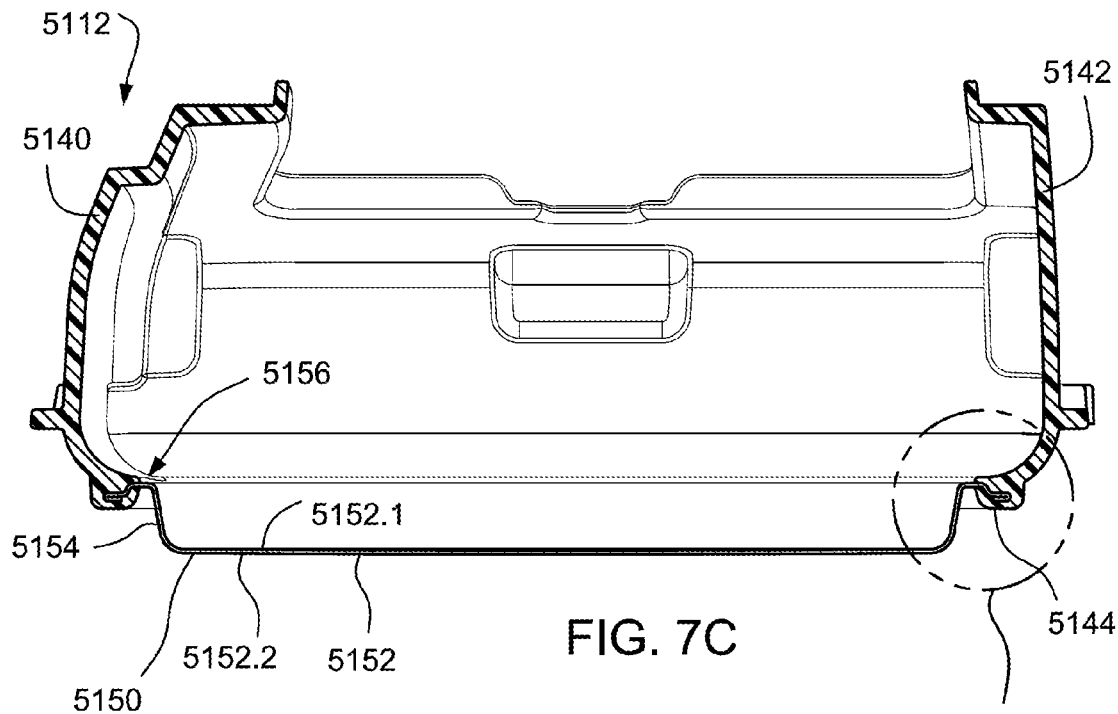
FIG. 7C is a cross-sectional view of the reservoir base of FIG. 7B according to an example of present technology.
Figure 7D:
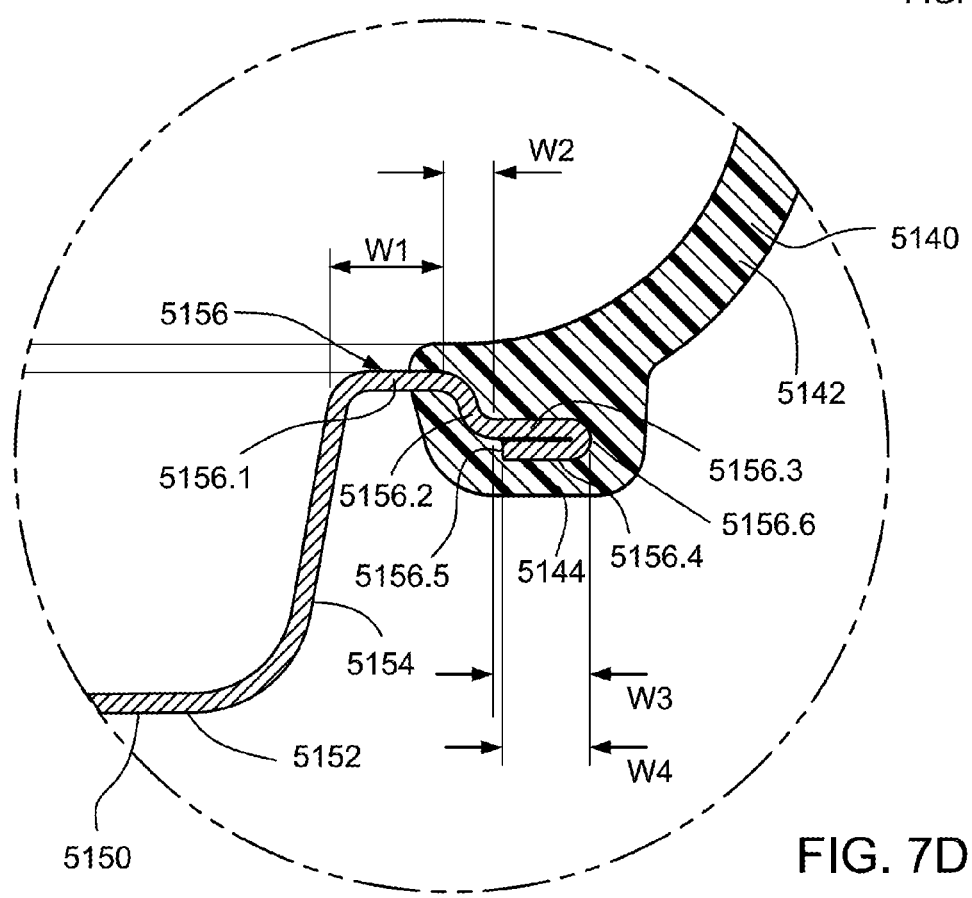
FIG. 7D is an enlarged view of a peripheral portion of the reservoir base of FIG. 7C.

As shown in FIGS. 7C and 7D, the metal conductive portion 5150 includes an interfacing portion 5156 according to an example of the present technology that is structured and arranged to secure the metal conductive portion 5150 to the plastic material main body 5140 while reducing or eliminating stress concentration between the metal conductive portion 5150 and the plastic material main body 5140.

As illustrated, the metal conductive portion 5150 includes a generally planar bottom wall or plate 5152, a side wall 5154 extending around the perimeter of the plate 5152, and an interfacing portion 5156 to secure the metal conductive portion 5150 to the plastic material main body 5140. The length/width of side wall 5154 may be approximately between 2 mm and 2 cm, e.g., or more specifically between 5 and 10 mm.

In the illustrated example, the plate 5152 includes a circular shape (e.g., see FIG. 7B), however other suitable shapes are possible, e.g., rectangular, square, oval. The shape of the plate 5152 may or may not correspond to a shape of the heater plate 5120. As illustrated, the plate 5152 includes a first side 5152.1 adapted to form a bottom interior surface of the reservoir 5110 exposed to the water. The plate 5152 includes a second side 5152.2, opposite to the first side 5152.1, adapted to form a bottom exterior surface of the reservoir 5110 exposed to the heater plate 5120, e.g., second side 5152.2 of the plate 5152 provides a contact surface structured and arranged to directly engage with the heater plate 5120. In an alternative example, the plate 5152 may comprise a non-planar shape.

The interfacing portion 5156 extends laterally outwardly from the side wall 5154 and into a thickness of the bottom wall 5144 of the main body 5140. The interfacing portion 5156 provides the connection or attachment between the metal conductive portion 5150 and the plastic material main body 5140.

In the illustrated example of FIG. 7D, the interfacing portion 5156 includes inner portion 5156.1 extending from the side wall 5154, a sloped portion 5156.2 extending from the inner portion 5156.1 to an intermediate portion 5156.3, and an end portion 5156.4 extending from the intermediate portion 5156.3. In an example, the width W1 (in radial direction) of the inner portion 5156.1 is about 1-5 mm, the width W2 of the sloped portion 5156.2 is about 0.5-2 mm, the width W3 of intermediate portion 5156.3 is about 1-5 mm, and the width W4 of the end portion 5156.4 is less than about 5 mm (e.g., 1-3 mm).

As illustrated, the sloped portion 5156.2 creates an offset between the inner portion 5156.1 and the intermediate portion 5156.3 so that the inner portion 5156.1 is out of plane, e.g., parallel, with the intermediate portion 5156.3. Such arrangement creates a mechanical interlock, e.g., an undercut, to prevent stripping or pull-out of the interfacing portion 5156 from the bottom wall 5144 of the main body 5140.

As illustrated, the end portion 5156.4 is rolled or curled underneath the intermediate portion 5156.3 so that the end portion 5156.4 and the intermediate portion 5156.3 are adjacent to one another, e.g., the end portion 5156.4 and the intermediate portion 5156.3 are generally parallel and flush to one another. Such arrangement moves any sharp edge or burr at the edge 5156.5 of the end portion 5156.4 into a non-critical area underneath the intermediate portion 5156.3, which at least reduces or eliminates stress concentration due to any sharp edge or burr. It should be noted that the area below the intermediate portion 5156.3 is considered less critical because it is located further away from the water facing surface of the bottom wall 5144. For that reason, even a small downwardly directed angle of bending of the end portion 5156.4 with respect to the intermediate portion 5156.3, is expected to move the burr further into the less risky zone in the lower part of the bottom wall 5144, and therefore reduce the risk of leakage, even if stress caused by the burr leads to a crack in the bottom wall 5144. With this regard, the larger the downward angle of the bending, the smaller the risk of leakage is. The configuration shown in FIG. 7D, where the end portion 5156.4 and the intermediate portion 5156.3 are generally parallel and flush to one another, is expected to carry the lowest risk of stress concentration and crack propagation and therefore the lowest risk of water leak. This is especially the case when the burr is formed on the inner edge of the end portion 5156.4, which in this full-hem configuration is in contact with the intermediate portion 5156.3. Since, during the hemming process, this inner surface of the end portion 5156.4 is depressed against the lower surface of the intermediate portion 5156.3, the burr is squashed, thus no longer posing any danger to the integrity of the bottom wall 5144.

Apart from the burr formed during the cutting process of edge 5156.5, there is another mechanical feature that may increase the risk of cracks in the bottom wall 5144. As can be seen in FIGS. 8A to 8C showing an exemplary processing method, the hemming process can include three stages, e.g., a first stage including bending of (also referred to as reclining) the end portion 5156.4 at 90 degrees with respect to the intermediate portion 5156.3 (FIG. 8A), a second stage including bending the end portion 5156.4 a further 30-60 degrees with respect to the intermediate portion 5156.3 (FIG. 8B), and a third stage including full bending (full hem) of the end portion 5156.4 to 180 degrees with respect to the intermediate portion 5156.3 (FIG. 8C). The first stage may also include bending of the inner portion 5156.1 relative to the side wall 5154, bending of the sloped portion 5156.2 relative to the inner portion 5156.1, and bending of the intermediate portion 5156.3 relative to the sloped portion 5156.2. The first stage is often performed within a punching die PD (see FIG. 8A), which leaves tool marks on the external surface, which can be a potential cause of stress, cracks and leaks. Whilst these marks are being referred to as "tool marks", they may be caused not only by the tool (by the dragging/friction forces of the die wall during bending), but also by the fact that large peripheral surface of the base metal plate is squeezed into a smaller circumference or perimeter during the bending process. These marks are always on the external surface. For example, in FIG. 7D, the hemming process may leave such marks on the lower (outer) surface of the end portion 5156.4. This is not accidental as the hemming and molding processes are preferably performed so that the marks are left on the metal plate surface which, when molded within the bottom wall 5144, points downwardly and away from the critical zone close to the water facing surface of the bottom wall 5144.

As described above, the bending of the end portion 5156.4 downwardly with respect to the intermediate portion 5156.3 at a progressively increasing angle is expected to bring a progressively smaller risk of leak-causing cracks caused by the burr. It should be noted that in the configuration of FIG. 7D, it is the lower surface of the end portion 5156.4 that may carry any tool marks. Thus, bending the end portion 5156.4 at a progressively increasing angle downwardly will also move any such tool marks away from the critical zone close to the water facing surface of the bottom wall 5144.

Figure 7E:
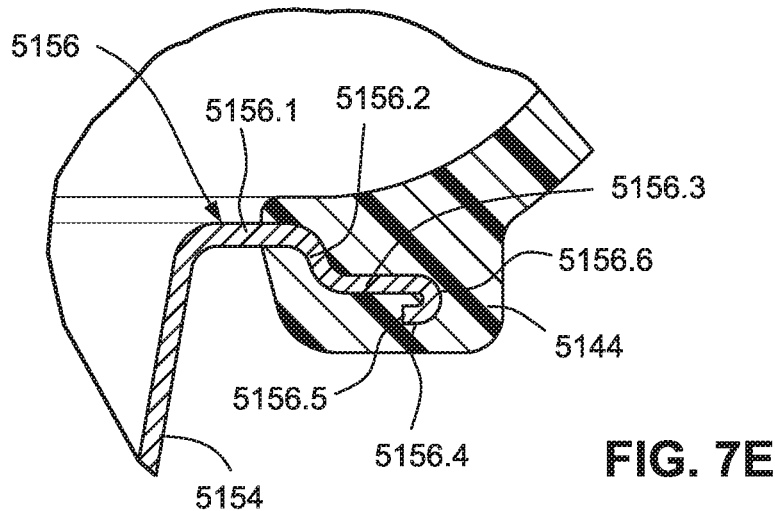
FIG. 7E is a cross-sectional view of a peripheral portion of the reservoir base according to another example of present technology.
Figure 7F:
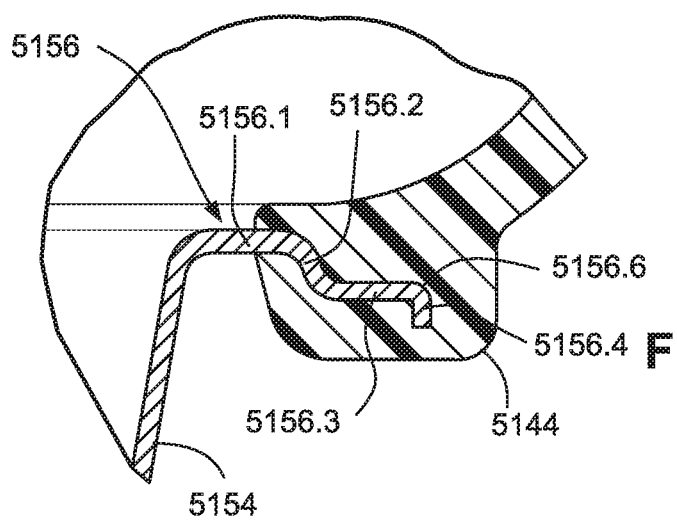
FIG. 7F is a cross-sectional view of a peripheral portion of the reservoir base according to another example of present technology.
Figure 7G:
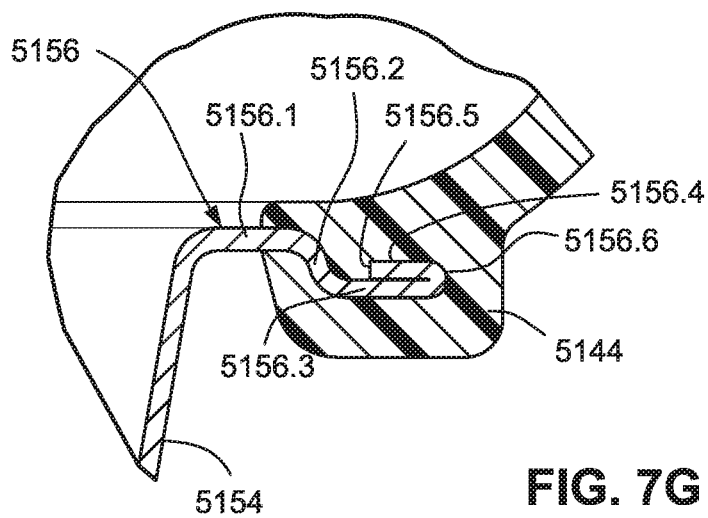
FIG. 7G is a cross-sectional view of a peripheral portion of the reservoir base according to another example of present technology

In another example, as shown in FIG. 7G, the end portion 5156.4 may not be curled underneath the intermediate portion 5156.3, but be curled above or over the intermediate portion 5156.3 so that the end portion 5156.4 is located closer to the water facing surface of the bottom wall 5144 than the intermediate portion 5156.3.

FIGS. 9A to 9C show an exemplary hemming process for the interfacing portion 5156 of FIG. 7G, e.g., a first stage including bending (reclining) of the end portion 5156.4 upwards at 90 degrees with respect to the intermediate portion 5156.3 (FIG. 9A), a second stage including bending the end portion 5156.4 a further 30-60 degrees with respect to the intermediate portion 5156.3 (FIG. 9B), and a third stage including full bending (full hem) of the end portion 5156.4 to 180 degrees with respect to the intermediate portion 5156.3 (FIG. 9C). The first stage may also include bending of the inner portion 5156.1 relative to the side wall 5154, bending of the sloped portion 5156.2 relative to the inner portion 5156.1, and bending of the intermediate portion 5156.3 relative to the sloped portion 5156.2. The first stage is often performed within a punching die PD (see FIG. 9A).

The interfacing portion 5156 of FIG. 7G (and associated hemming process of FIGS. 9A to 9C) is different than that of FIG. 7D as it includes bending in an upward direction and towards the more critical water facing surface of the bottom wall 5144. In this case, any tool marks associated with an outer bending surface, and any burrs associated with the cutting edge 5156.5, get closer to the water facing surface of the bottom wall 5144. In this case, regardless of which end of the edge 5156.5 the burr is on, the larger the upward bending angle, the larger the risk that any cracks caused by the burr or by the marks, may cause leakage. Only when the burr is on the upper side and the angle is sufficiently large that the configuration is close to a full hem, can the risk of leak be mitigated significantly. Especially advantageous again is the case of full-hem, when the surface of end portion 5156.4 with the burr is depressed against the upper surface of the intermediate portion 5156.3, the burr is squashed and its stress inducing effect mitigated. At the same time, the tool marks will also be mitigated, as the surface with these marks is the one that, in this full-hem configuration, is in contact with the upper surface of the intermediate portion 5156.3.

One process that provides an alternative way of removing the burr and reducing stress concentration is electro polishing of the edge 5156.5 of the conductive metal plate. However, during the process, the metal plate usually needs to be held in several places and some burrs may remain at point of contact. Another alternative process includes linishing, but this process may lack consistency over a large number of samples.

In an example, such rolled end portion 5156.4 may be a hem formed by a hemming metal-forming process as described above, e.g., see FIGS. 8A to 8C and 9A to 9C. Also, in some cases, the rolled end 5156.6 provided by the hem may be provided with a relatively large outer radius or curvature to avoid stress concentration. It is assumed that any radius that is equal or large than the thickness of the metal sheet will be sufficient to avoid creating stress in the bottom wall of the main body in the vicinity of the hem.

In an alternative example, as shown in FIG. 7E, the end portion 5156.4 and the intermediate portion 5156.3 of the hem may not be completely flush, e.g., a space or pocket may be provided between the end portion 5156.4 and the intermediate portion 5156.3. Also, even though the end portion 5156.4 includes a similar length to the intermediate portion 5156.3 in FIG. 7D, this does not have to be the case. For example, the end portion 5156.4 and the intermediate portion 5156.3 may have different lengths with respect to one another, as shown in FIG. 7E where the end portion 5156.4 includes a shorter length than the intermediate portion 5156.3. In an example, the rolled end portion 5156.4 in FIG. 7E may be a curl formed by a curling metal-forming process. Again, the rolled end 5156.6 provided by the curl may include a relatively large outer radius or curvature to avoid stress concentration.

In another example, as shown in FIG. 7F, the end portion 5156.4 may not be "curled", but be bent relative to the intermediate portion 5156.3 so that the end portion 5156.4 extends at an angle to the intermediate portion 5156.3. In the illustrated example, the end portion 5156.4 extends about 90° to the intermediate portion 5156.3, however it should be appreciated that other suitable angles are possible. Whilst acute angles are also believed acceptable, it is believed that any downward pointing angles close to, and especially larger than, 90 degrees are more beneficial. In an example, the bent end portion 5156.4 in FIG. 7F may be formed by a bending metal-forming process. Also, the bent end 5156.6 provided by the bend includes a relatively large outer radius or curvature to avoid stress concentration.

Further configurations of the metal conductive portion 5150 are also possible. For example, as shown in FIG. 7G described above, the end portion 5156.4 may be curled/bent backwards so it can be directed above the intermediate portion 5156.3, and not under as shown in FIGS. 7D to 7F. It should be appreciated that "above" and "under" here refer to relative directions defined in relation to the operative configuration of the tub of which metal conductive portion 5150 forms part of. As discussed above, the "above" configuration of FIG. 7G may be less advantageous than the "under" configuration of FIGS. 7D to 7F because the burr is moved from the less-critical area at the lower part of the bottom wall 5144 (which is further away from the water inside the tub) into the more critical area of the upper portion of the bottom wall 5144, which area is closer to the water in the operative configuration of the tub. One exception is the configuration where the upward angle is close to 180 degrees, which may completely crush the burr, if the burr is on the upper surface of the end portion 5156.4. As this "upper" surface is in this case the inner surface for the bend, the burr is crushed between the two folded surfaces. Such a configuration, where the angle is close to 180 degrees, is referred here as a full-hem configuration, and may also be advantageous for mitigating the risk of leak.

Another aspect of the present technology relates to improving the seal between a metal conductive portion 5150 and the hard plastic material of the main body 5140, with which the peripheral interfacing portion 5156 is mechanically engaged. The improved sealing limits the ingress of water to the peripheral interfacing portion 5156. The limited access of water to the peripheral interfacing portion 5156 of the metal conductive portion 5150 reduces the likelihood of leak, as well as reduces the likelihood of oxidation of the peripheral interfacing portion 5156 of the metal conductive portion 5150, thereby enhancing the lifetime of the reservoir base 5112.

Figure 10A:
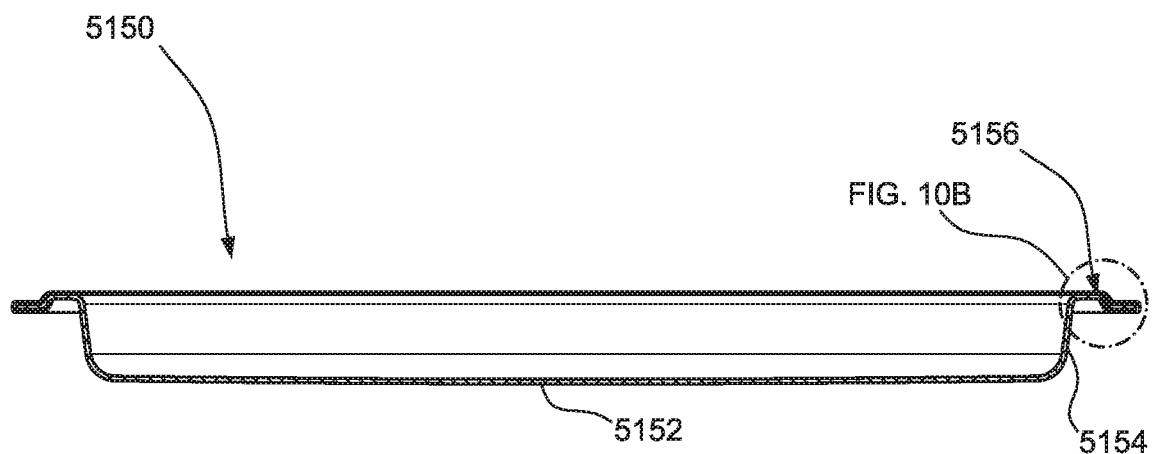
FIG. 10A is a cross-sectional view of a conductive portion for a reservoir base of a humidifier reservoir according to an example of present technology.
Figure 10B:
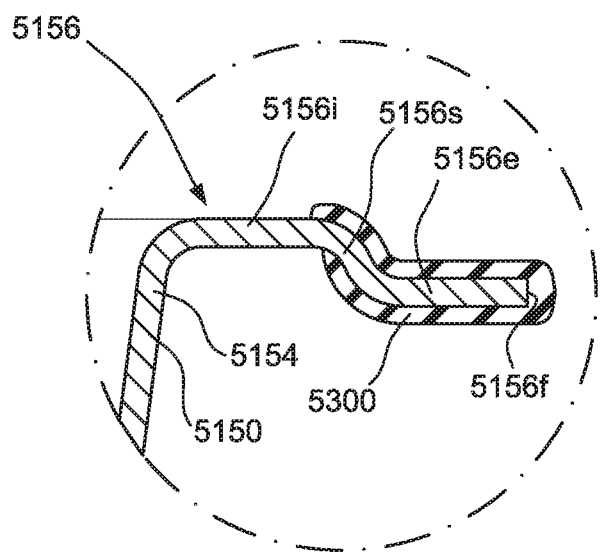
FIG. 10B is an enlarged view of a portion of the conductive portion of FIG. 10A.
Figure 11A:
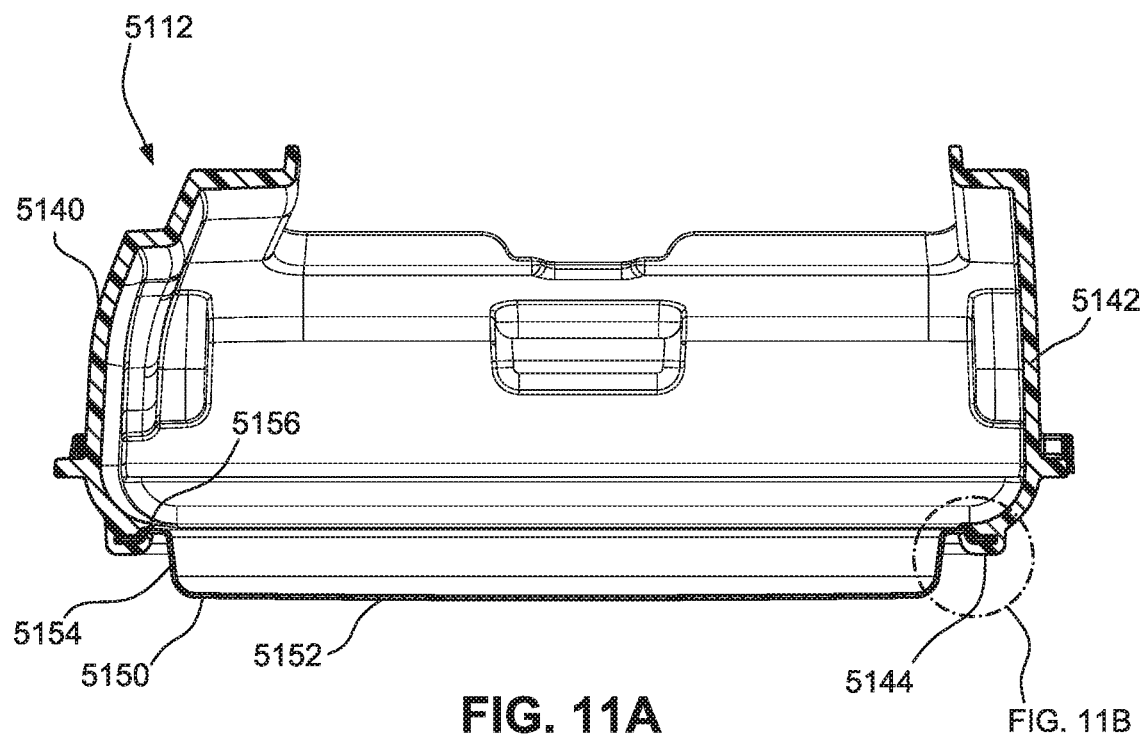
FIG. 11A is a cross-sectional view of a reservoir base of a humidifier reservoir according to an example of present technology.
Figure 11B:
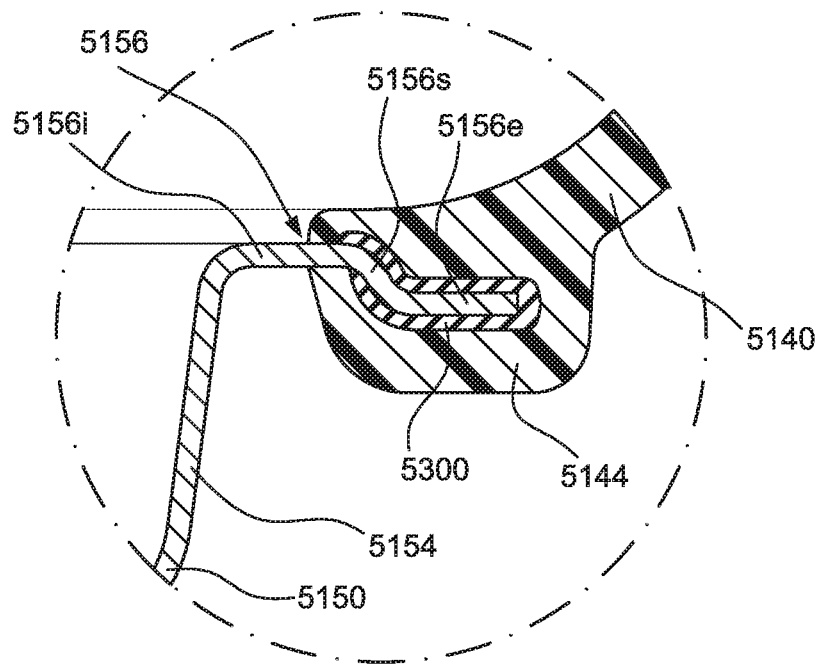
FIG. 11B is an enlarged view of a portion of the reservoir base of FIG. 11A.

FIGS. 10A to 10B show a metal conductive portion 5150 with a silicone overmold 5300 according to an example of the present technology, and FIGS. 11A to 11B show such metal conductive portion 5150 with a silicone overmold 5300 provided to a reservoir base 5112 according to an example of the present technology.

As shown in FIGS. 10A and 10B, the metal conductive portion 5150 includes a generally planar bottom wall or plate 5152, a side wall 5154 extending around the perimeter of the plate 5152, and an interfacing portion 5156 to secure the metal conductive portion 5150 to the plastic material main body 5140.

The interfacing portion 5156 extends laterally outwardly from the side wall 5154 and into a thickness of the bottom wall 5144 of the main body 5140. The interfacing portion 5156 provides the connection or attachment between the metal conductive portion 5150 and the plastic material main body 5140.

In the illustrated example of FIGS. 10A and 10B, the interfacing portion 5156 includes inner portion 5156*i* extending from the side wall 5154, an end portion 5156*e*, and a sloped portion 5156*s* extending from the inner portion 5156*i* to the end portion 5156*e*. The sloped portion 5156*s* creates an offset between the inner portion 5156*i* and the end portion 5156*e* so that the inner portion 5156*i* is out of plane with the end portion 5156*e*, thus improving the retention of the interfacing portion 5156 of the metal conductive portion 5150 within the hard plastic material of the main body 5140. According to an example of the present technology, a silicone overmold 5300 is provided to the interfacing portion 5156 and configured to wrap around and cover exterior surfaces of at least a portion of the end portion 5156*e* (including the end face 5156*f* at the free end of the end portion 5156*e*). This does not have to be the case and the silicone overmold 5300 may be located only on limited area of the upper surface (as viewed in FIGS. 10B and 11B) of the interfacing portion 5156 and cover only a limited portion of this upper surface. In the illustrated configuration, the silicone overmold 5300 covers both exterior upper and lower surfaces of the entire end portion 5156*e*, the entire sloped portion 5156*s*, and even a portion of the inner portion 5156*i*. The additional silicone overmold 5300 preferably covers as much of the length of the interfacing portion 5156 as possible to provide further protection from oxidation and improved sealing at the interface between the metal conductive portion 5150 and the plastic material main body 5140. The silicone overmold 5300 however should preferably not protrude outside the plastic material main body 5140 (e.g., see FIG. 11B which shows how the silicone overmold 5300 is contained within the plastic material main body 5140), as such a protrusion outside the plastic material main body 5140 will interfere with the manufacturing process of the reservoir base.

In an example, the metal conductive portion 5150 may be pre-formed, the silicone overmold 5300 may be overmolded over at least a portion of the interfacing portion 5156 of the metal conductive portion 5150, and then the plastic material main body 5140 may be overmolded over the interfacing portion 5156 of the metal conductive portion 5150 and the silicone overmold 5300 thereof.

For example, the metal conductive portion 5150 is first formed into its working configuration by one or more metal-forming processes, e.g., press metal forming. One or more secondary processes may follow the one or more metal forming processes, e.g., electro-polishing (chemical process) to remove burrs from the metal conductive portion 5150 and passivation to improve resistance to oxidation. Following the one or more metal-forming processes and the one or more secondary processes, silicone is then overmolded over a portion of the interfacing portion 5156 of the metal conductive portion 5150 to form the silicone overmold 5300 (e.g., see FIGS. 10A and 10B). Referring to FIGS. 10B and 11B, the portion of the interfacing portion 5156 mentioned here is with reference to the radial direction. The silicone material for the silicone overmold 5300 comprises a silicone grade with a suitable bond strength for connection with the metal conductive portion 5150.

Then, the plastic material main body 5140 is overmolded over the interfacing portion 5156 of the metal conductive portion 5150 and the silicone overmold 5300 thereof (e.g., see FIGS. 11A and 11B). In an example, the metal conductive portion 5150 and silicone overmold 5300 thereof (i.e., the insert) is inserted into an injection mold for the main body 5140 prior to injection of molten plastic material into the injection mold. During the injection process, the molten plastic material flows around the interfacing portion 5156 and the silicone overmold 5300, and locks or connects the metal conductive portion 5150 to the main body 5140 as the molten plastic material solidifies. The additional silicone overmold 5300 preferably covers as much of the length of the interfacing portion 5156 as possible, without protruding outside the plastic material main body 5140, to facilitate blanking off the metal plate during the overmolding process of the plastic material main body 5140. From this point of view, one way of deciding on how much inwardly (in radial direction, in the case of a circular metal plate, as illustrated in FIG. 7B) should the silicone overmold 5300 extend may be by first considering how much of the interfacing portion 5156 should be engaged with the plastic material main body 5140.

The silicone overmold 5300, provided to surfaces of the interfacing portion 5156 before the metal conductive portion 5150 is inserted into the injection mold, provides further protection from oxidation and enhanced sealing. Because the silicone overmold 5300 is already cured before the second overmolding process, there is no strong chemical bond between the silicone overmold 5300 and the overmolded plastic material of the main body 5140. However, when the hard plastic of the main body 5140 shrinks during the curing process at the end of the second overmolding, it compresses the underlying flexible silicone overmold 5300. This compression and the flexible nature of the silicone overmold 5300 seals any gaps between the two interfaces (i.e., (1) the one between the metal conductive portion 5150 and the silicone overmold 5300 and (2) the one between the silicone overmold 5300 and the plastic of main body 5140) thereby making the two interfaces substantially watertight. Other fastening processes, such as ultrasonic welding, may also be used to attach the main body 5140 to the interfacing portion 5156. However, such techniques need at least two plastic parts to sandwich the interfacing portion 5156 and may have less uniform control and/or distribution of the compression force, which may cause displacement of the silicone overmold during welding in some areas of the periphery of the metal plate. This may result in less than sufficient compression in some peripheral areas and may negatively affect the overall sealing performance.

The two staged overmolding process (i.e., (1) overmolding the silicone overmold 5300 over the interfacing portion 5156 of the metal conductive portion 5150 and (2) overmolding the main body 5140 over the silicone overmold 5300) offers a more robust water seal, with improved manufacturing convenience, efficiency and cost savings.

Figure 12:
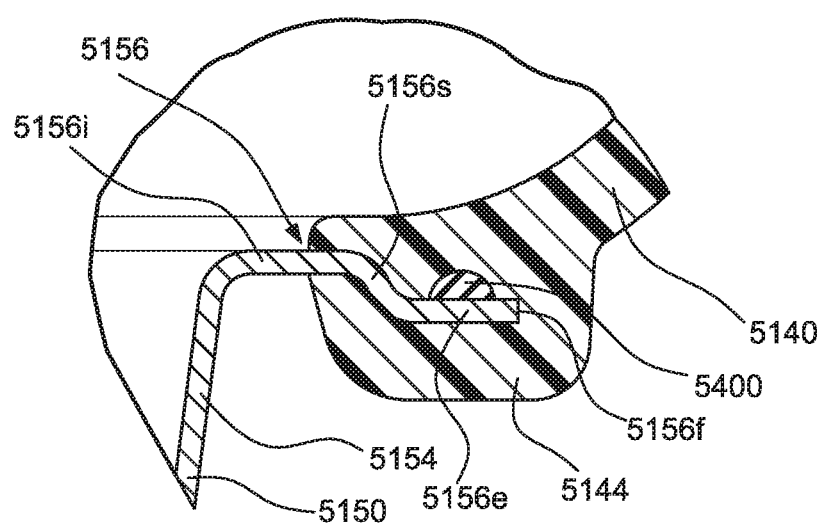
FIG. 12 is a cross-sectional view of a peripheral portion of the reservoir base of a humidifier reservoir according to another example of present technology.

While the example illustrated in FIGS. 10A to 11B is described with reference to a large portion of the interfacing portion 5156 being enclosed by the silicone overmold 5300 (FIGS. 10A to 11B), it should be appreciated that a silicone, or other sealing material (overmolded or otherwise) may be provided in other configurations to the interfacing portion 5156 of a metal conductive portion 5150 (e.g., see FIG. 7C) to improve sealing and increase the resistance to oxidation. For example, FIG. 12 shows a cross-sectional view of an arrangement where a continuous bead 5400 of a silicone material (in this case with a semi-circular cross-section) has been dispensed only on a portion of the upper exterior surface of the end portion 5156e along the periphery of the interfacing portion 5156. The plastic material of the main body 5140 is then overmolded over the interfacing portion 5156 and the silicone bead 5400. Whilst water (which in the figure is located in the space above the metal plate) can reach a portion of the interfacing portion 5156 that is upstream (i.e., to the left as viewed in FIG. 12) of the silicone bead 5400, the silicone bead 5400 creates a barrier to the further penetration of water and protects the downstream portions of the interfacing portion 5156 (which covers the end face 5156f at the free end of the end portion 5156e and the underside or lower exterior surface of the peripheral interfacing portion 5156) from corrosion and water leak. In an example, the higher upstream the silicone bead 5400 is disposed (i.e., towards the sloped portion 5156s and the inner portion 5156i), the larger portion of the interfacing portion 5156 is protected from water ingress.

Thus, one or more sealing materials, such as silicone or other materials, can be overmolded, or otherwise dispensed, over at least a portion of the interfacing portion 5156, over which the main body 5140 is then overmolded. For example, similar sealing effect may be achieved if the interfacing portion 5156 of the metal conductive portion 5150 is dipped into a melted plastic or rubber material.

Alternatively, instead of using the above described sealing effect of a compressed flexible material that has been overmolded or otherwise dispensed, adhesion promoters, powder coatings, enamel coatings, epoxy materials, foam gasket materials, etc. can be dispensed over the interfacing portion 5156 to enhance the bond and seal between the interfacing portion 5156 and the main body 5140.

In addition, the illustrated examples are provided with reference to FIGS. 7D to 7G and 11B where the interfacing portion 5156 of the conductive portion 5150 is engaged with a bottom wall 5144 of the main body 5140. However, it should be appreciated that other configurations are possible. For example, in another configuration, the conductive portion 5150 may comprise the entire bottom of the water reservoir. In this case, it may be considered that the peripheral edge of the conductive portion 5150 is engaged not with a bottom wall, but with one or more side walls of the main body of the water reservoir.

5.6.2.3 Humidifier Reservoir Dock

In one form, the humidifier 5000 may comprise a humidifier reservoir dock 5130 (as shown in FIGS. 4A to 4C) configured to receive the humidifier reservoir 5110. In some arrangements, the humidifier reservoir dock 5130 may comprise a locking feature configured to retain the reservoir 5110 in the humidifier reservoir dock 5130.

5.6.2.4 Water Level Indicator

The humidifier reservoir 5110 may comprise a water level indicator. In some forms, the water level indicator may provide one or more indications to a user such as the patient 1000 or a care giver regarding a quantity of the volume of water in the humidifier reservoir 5110. The one or more indications provided by the water level indicator may include an indication of a maximum, predetermined volume of water, any portions thereof, such as 25%, 50% or 75% or volumes such as 200 ml, 300 ml or 400 ml.

5.6.2.5 Humidifier Transducer(s)

Figure 13:
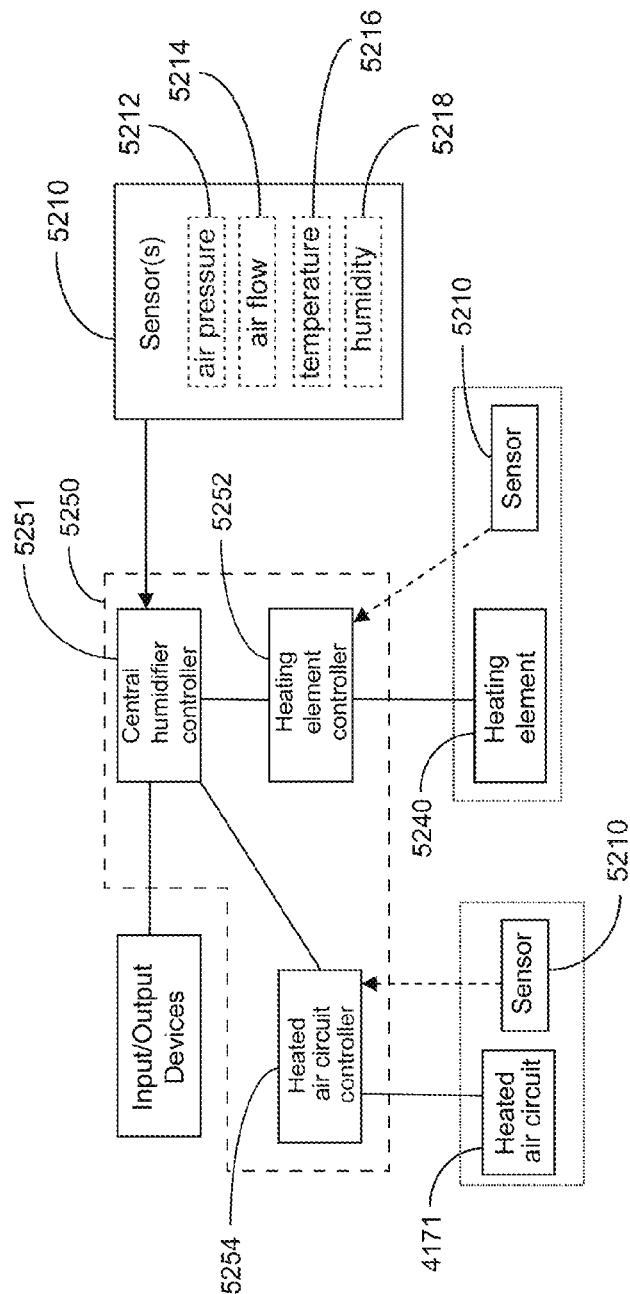
FIG. 13 shows a schematic of a humidifier.

As shown in FIG. 13, the humidifier 5000 may comprise one or more humidifier transducers (sensors) 5210 instead of, or in addition to, transducers provided in the RPT device 4000. Humidifier transducers (sensors) 5210 may include one or more of an air pressure transducer/sensor 5212, an air flow rate transducer/sensor 5214, a temperature transducer/sensor 5216, or a humidity transducer/sensor 5218 as shown in FIG. 13. A humidifier transducer (sensor) 5210 may produce one or more output signals which may be communicated to a controller such as the central controller of the RPT device 4000 and/or a central humidifier controller 5250. In some forms, a humidifier transducer may be located externally to the humidifier 5000 (such as in the air circuit 4170) while communicating the output signal to the controller. Each of the reference numbers 5210-5218 is used to refer to both the respective transducer, as well as the overall sensor, which usually includes further electronic circuitry to facilitate the management and processing of the data generated by the respective transducer.

5.6.2.5.1 Pressure Transducer

One or more pressure transducers 5212 may be provided to the humidifier 5000 in addition to, or instead of, a pressure sensor provided in the RPT device 4000.

5.6.2.5.2 Flow Rate Transducer

One or more flow rate transducers 5214 may be provided to the humidifier 5000 in addition to, or instead of, a flow rate sensor provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base where heat may be provided to the humidifier reservoir 5110 primarily by conduction.

5.6.2.7 Humidifier Controller

According to one arrangement of the present technology, a humidifier 5000 may comprise a humidifier controller 5250 as shown in FIG. 13. In one form, the humidifier controller 5250 may be a part of a central controller of the RPT device 4000. In another form, the humidifier controller 5250 may be a separate controller, which may be in communication with a central controller of the RPT device 4000.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 13, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 GLOSSARY

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8 OTHER REMARKS

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 REFERENCE SIGNS LIST

| Feature Item | Number |
| --- | --- |
| patient | 1000 |
| bed partner | 1100 |
| patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| air circuit | 4170 |
| humidifier | 5000 |
| water reservoir | 5110 |
| reservoir base | 5112 |
| reservoir lid | 5114 |
| compliant portion | 5116 |
| inlet | 5118 |
| heater plate | 5120 |
| outlet | 5122 |
| reservoir dock | 5130 |
| orifice | 5138 |
| main body | 5140 |
| side walls | 5142 |
| bottom wall | 5144 |
| conductive portion | 5150 |
| bottom wall | 5152 |
| first side | 5152.1 |
| second side | 5152.2 |
| side wall | 5154 |
| interfacing portion | 5156 |
| inner portion | 5156.1 |
| sloped portion | 5156.2 |
| intermediate portion | 5156.3 |
| end portion | 5156.4 |
| edge | 5156.5 |
| end | 5156.6 |
| end portion | 5156e |
| end face | 5156f |
| inner portion | 5156i |
| sloped portion | 5156s |
| hinges | 5158 |
| cavity | 5160 |
| dock air outlet | 5168 |
| dock air inlet | 5170 |
| humidifier outlet | 5172 |
| humidifier transducer (sensor) | 5210 |
| pressure transducer (sensor) | 5212 |
| flow rate transducer (sensor) | 5214 |
| temperature transducer (sensor) | 5216 |
| humidity sensor | 5218 |
| inner lip | 5224 |
| outer lip | 5226 |
| heating element | 5240 |
| humidifier controller | 5250 |
| central humidifier controller | 5251 |
| heating element controller | 5252 |
| air circuit controller | 5254 |
| silicone overmold | 5300 |
| silicone bead | 5400 |
| metal | M |
| punch | P |
| burr | B |
| crack | C |
| plastic material portion | PP |
| metal plate | MP |

The invention claimed is:

1. A water reservoir for an apparatus for humidifying a flow of breathable gas, comprising:
    a reservoir body forming a cavity structured to hold a volume of liquid,
    the reservoir body comprising a conductive portion provided at a lower portion of the reservoir body,
    wherein the conductive portion comprises a thermally conductive material and is configured to thermally engage with a heater plate to allow thermal transfer of heat from the heater plate to the volume of liquid,
    wherein the conductive portion includes a substantially planar bottom wall, a side wall extending around a perimeter of the bottom wall, and a peripheral interfacing portion that extends outward from the side wall,
    wherein the peripheral interfacing portion is structured and arranged to connect the conductive portion to one or more walls of the reservoir body,
    wherein the peripheral interfacing portion includes an inner portion extending from the side wall, a sloped portion extending from the inner portion, an intermediate portion extending from the sloped portion, and an end portion extending from the intermediate portion, and
    wherein the end portion is bent so as to be at least partly inclined in a downward direction with respect to the intermediate portion to reduce a risk of leakage caused by cracks within the one or more walls due to a presence of an edge at the end portion.

2. The water reservoir according to claim 1, wherein inclination of the end portion is at an angle of substantially 180 degrees so that the end portion and the intermediate portion are generally parallel to one another.

3. The water reservoir according to claim 1, wherein the end portion and the intermediate portion are generally flush to one another.

4. The water reservoir according to claim 1, wherein the peripheral interfacing portion is structured and arranged to sealingly connect the conductive portion to the one or more walls of the reservoir body.

5. The water reservoir according to claim 1, wherein the conductive portion comprises a metallic material.

6. The water reservoir according to claim 1, wherein the one or more walls comprises a bottom wall and the conductive portion is connected to a bottom wall of the reservoir body.

7. The water reservoir according to claim 1, wherein the end portion is inclined away from a water facing surface of the one or more walls of the reservoir body.

8. The water reservoir according to claim 1, wherein the end portion is inclined with respect to the intermediate portion so that an external surface of the end portion, and any one or more tool marks thereof, are oriented away from a critical area of the one or more walls of the reservoir body.

9. The water reservoir according to claim 1, wherein the end portion is inclined towards a water facing surface of the one or more walls of the reservoir body.

10. The water reservoir according to claim 1, wherein the end portion is inclined with respect to the intermediate portion at an angle of inclination larger than 90 degrees.

11. The water reservoir according to claim 1, wherein the end portion is rolled or curled relative to the intermediate portion to provide the end portion with a radius or curvature.

12. The water reservoir according to claim 1, wherein the substantially planar bottom wall includes a circular shape.

13. The water reservoir according to claim 1, wherein the sloped portion creates an offset between the inner portion and the intermediate portion so that the inner portion is out of plane with the intermediate portion.

14. The water reservoir according to claim 1, wherein the reservoir body comprises a main body comprising a plastic material, and the conductive portion comprises an insert molded construction with the main body.

15. The water reservoir according to claim 14, wherein the reservoir body comprises a two-part construction comprising only the main body and the conductive portion.

16. The water reservoir according to claim 1, further comprising a reservoir lid movably connected to the reservoir body to allow the water reservoir to be convertible between an open configuration and a closed configuration.

17. An apparatus for humidifying a flow of breathable gas, comprising:
    a water reservoir dock; and
    the water reservoir according to claim 1 provided to the water reservoir dock,
    wherein the water reservoir dock forms a cavity to receive the water reservoir, and the water reservoir dock includes the heater plate adapted to thermally engage the conductive portion provided to the water reservoir.

* * * * *